United States Patent
Prass

(10) Patent No.: US 7,214,197 B2
(45) Date of Patent: May 8, 2007

(54) INTRAOPERATIVE NEUROPHYSIOLOGICAL MONITORING SYSTEM

(76) Inventor: Richard L. Prass, 1009 Caton Dr., Virginia Beach, VA (US) 23454

( * ) Notice: Subject to any disclaimer, the term of this patent is extended or adjusted under 35 U.S.C. 154(b) by 866 days.

(21) Appl. No.: 09/985,708

(22) Filed: Nov. 6, 2001

(65) Prior Publication Data

US 2003/0088185 A1   May 8, 2003

(51) Int. Cl.
*A61B 5/05* (2006.01)
*A61B 5/04* (2006.01)
*A61N 1/00* (2006.01)

(52) U.S. Cl. ............ 600/554; 600/546; 600/547; 607/63

(58) Field of Classification Search ............ 600/544, 600/546, 547, 554; 607/63
See application file for complete search history.

(56) References Cited

U.S. PATENT DOCUMENTS

| | | | |
|---|---|---|---|
| 1,717,480 A | 6/1929 | Wappler |
| 2,110,735 A | 3/1938 | Marton |
| 2,516,882 A | 8/1950 | Kalom |
| 2,994,324 A | 8/1961 | Lemos |
| 3,035,580 A | 5/1962 | Guiorguiev |
| 3,057,356 A | 10/1962 | Greatbatch |
| 3,060,923 A | 10/1962 | Reiner |
| 3,087,486 A | 4/1963 | Kilpatrick |
| 3,147,750 A | 9/1964 | Fry |
| 3,212,496 A | 10/1965 | Preston |
| 3,313,293 A | 4/1967 | Chesebrough et al. |
| 3,580,242 A | 5/1971 | LaCroix |
| 3,651,812 A | 3/1972 | Samuels |
| 3,662,744 A | 5/1972 | Low et al. |
| 3,664,329 A | 5/1972 | Naylor |
| 3,682,162 A | 8/1972 | Colyer |
| 3,703,900 A | 11/1972 | Holznagel |
| 3,830,226 A | 8/1974 | Staub et al. |
| 3,857,398 A | 12/1974 | Rubin |
| 3,933,157 A | 1/1976 | Bjurwill et al. |
| 3,957,036 A | 5/1976 | Normann |
| 3,960,141 A | 6/1976 | Bolduc |
| 4,088,141 A | 5/1978 | Niemi |
| 4,099,519 A | 7/1978 | Warren |

(Continued)

OTHER PUBLICATIONS

Daniel M. Schwartz and Seth I. Rosenburg, "Facial Nerve Monitoring During Parotidectomy", Neuromonotinotim in Otology and Head and Neck Surgery, Chapter 6, pp. 121-130.

*Primary Examiner*—Max F. Hindenburg
*Assistant Examiner*—Jonathan Foreman

(57) ABSTRACT

An intraoperative neurophysiological monitoring system includes an adaptive threshold detection circuit adapted for use in monitoring with a plurality of electrodes placed in muscles which are enervated by a selected nerve and muscles not enervated by the nerve. Nerve monitoring controller algorithms permit the rapid and reliable discrimination between non-repetitive electromyographic (EMG) events repetitive EMG events, thus allowing the surgeon to evaluate whether nerve fatigue is rendering the monitoring results less reliable and whether anesthesia is wearing off. The intraoperative monitoring system is designed as a "surgeon's monitor," and does not require a neurophysiologist or technician to be in attendance during surgery. The advanced features of the intraoperative monitoring system will greatly assist neurophysiological research toward the general advancement of the field intraoperative EMG monitoring through post-surgical analysis. The intraoperative monitoring system is preferably modular, in order to allow for differential system pricing and upgrading as well as to allow for advances in computer technology; modularity can also aid in execution of the design.

25 Claims, 11 Drawing Sheets

U.S. PATENT DOCUMENTS

| | | | |
|---|---|---|---|
| 4,141,365 A | 2/1979 | Fischell et al. | |
| 4,155,353 A | 5/1979 | Rea et al. | |
| 4,177,799 A | 12/1979 | Masreliez | |
| 4,184,492 A | 1/1980 | Meinke et al. | |
| 4,200,104 A | 4/1980 | Harris | |
| 4,204,545 A | 5/1980 | Yamakoshi | |
| 4,233,987 A | 11/1980 | Feingold | |
| 4,235,242 A | 11/1980 | Howson et al. | |
| 4,294,245 A | 10/1981 | Bussey | |
| 4,308,012 A | 12/1981 | Tamler et al. | |
| 4,331,157 A | 5/1982 | Keller, Jr. et al. | |
| 4,372,319 A | 2/1983 | Ichinomiya et al. | |
| 4,374,517 A | 2/1983 | Hagiwara | |
| 4,402,323 A | 9/1983 | White | |
| 4,469,098 A | 9/1984 | Davi | |
| 4,483,338 A | 11/1984 | Bloom et al. | |
| 4,487,489 A | 12/1984 | Takamatsu | |
| 4,510,939 A | 4/1985 | Brenman et al. | |
| 4,515,168 A | 5/1985 | Chester et al. | |
| 4,517,976 A | 5/1985 | Murakoshi et al. | |
| 4,517,983 A | 5/1985 | Toyosu et al. | |
| 4,537,198 A | 8/1985 | Corbett | |
| 4,565,200 A | 1/1986 | Cosman | |
| 4,576,178 A | 3/1986 | Johnson | |
| 4,785,812 A | 11/1988 | Pihl et al. | |
| 4,807,643 A * | 2/1989 | Rosier | 600/554 |
| 4,817,628 A | 4/1989 | Zealear et al. | |
| 4,892,105 A | 1/1990 | Prass | |
| 4,920,968 A | 5/1990 | Takase | |
| 4,926,880 A | 5/1990 | Claude et al. | |
| 4,934,377 A | 6/1990 | Bova et al. | |
| 4,934,378 A | 6/1990 | Perry, Jr. | |
| 4,962,766 A | 10/1990 | Herzon | |
| 5,024,228 A | 6/1991 | Goldstone et al. | |
| 5,146,920 A | 9/1992 | Yuuchi et al. | |
| 5,161,533 A | 11/1992 | Prass et al. | |
| 5,215,100 A * | 6/1993 | Spitz et al. | 600/554 |
| 5,284,154 A | 2/1994 | Raymond et al. | |
| 5,560,372 A | 10/1996 | Cory | |
| 5,775,331 A | 7/1998 | Raymond et al. | |
| 6,181,961 B1 | 1/2001 | Prass | |
| 6,292,701 B1 | 9/2001 | Prass et al. | |
| 6,334,068 B1 * | 12/2001 | Hacker | 600/545 |
| 2001/0031916 A1 * | 10/2001 | Bennett et al. | 600/383 |

* cited by examiner

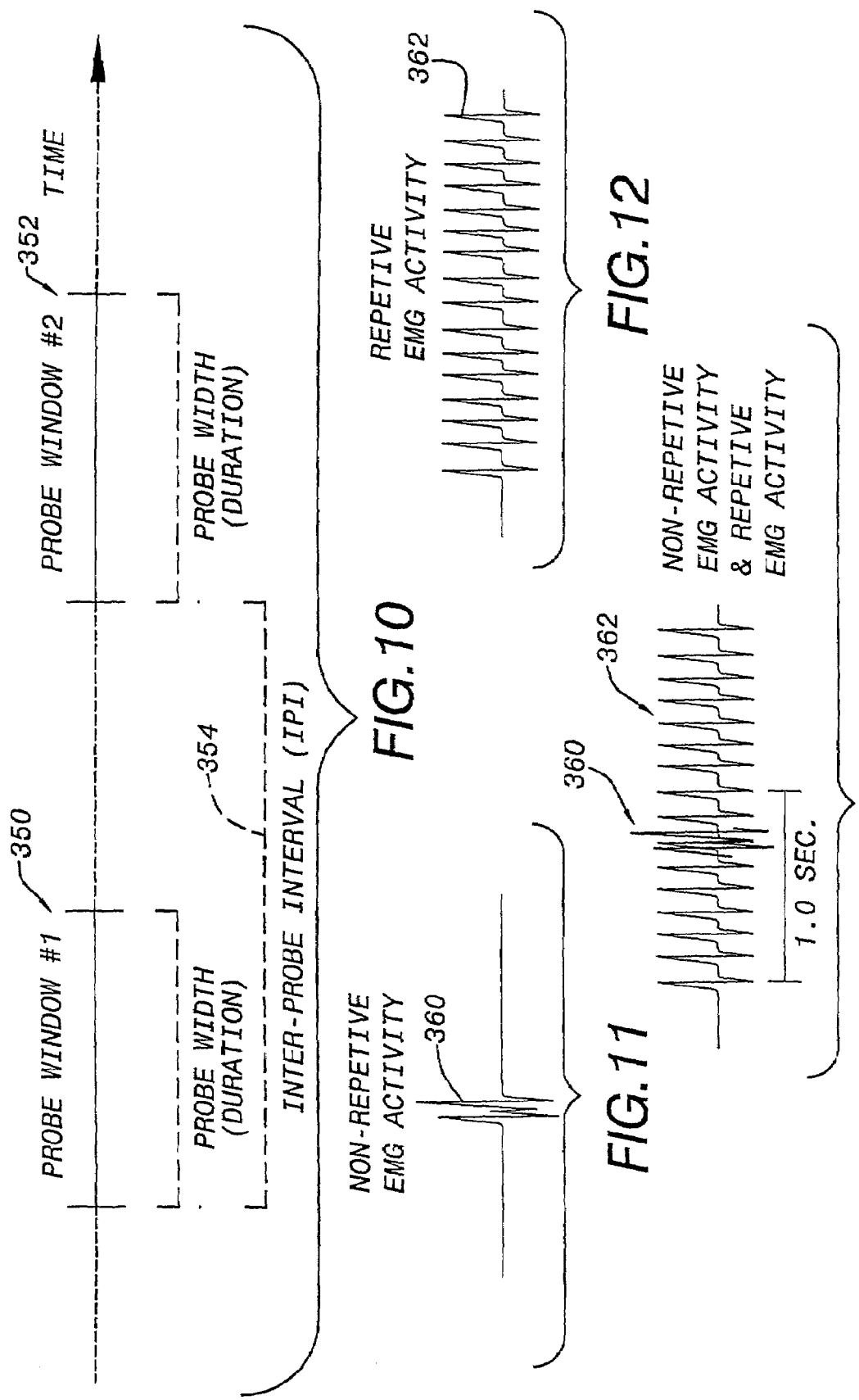

INTRAOPERATIVE NEUROPHYSIOLOGICAL MONITORING SYSTEM

BACKGROUND OF THE INVENTION

1. Field of the Invention

The present invention relates to surgical apparatus and more particularly to a neurophysiological monitoring system including a nerve integrity monitoring instrument for use in conjunction with one or more electrical stimulus probes as an intraoperative aid in defining the course of neural structures. The invention is particularly applicable for use in monitoring facial electromyographic (EMG) activity during surgeries in which a facial motor nerve is at risk due to unintentional manipulation, although it will be appreciated that the invention has broader applications and can be used in other neural monitoring procedures.

2. Discussion of the Prior Art

Despite advances in diagnosis, microsurgical techniques, and neurotological techniques enabling more positive anatomical identification of facial nerves, loss of facial nerve function following head and neck surgery such as acoustic neuroma resection is a significant risk. Nerves are very delicate and even the best and most experienced surgeons, using the most sophisticated equipment known, encounter a considerable hazard that a nerve will be bruised, stretched or severed during an operation. Studies have shown that preservation of the facial nerve during acoustic neuroma resection may be enhanced by the use of intraoperative electrical stimulation to assist in locating nerves. Very broadly stated, the locating procedure, also known as nerve integrity monitoring, involves inserting sensing or recording electrodes directly within cranial muscles enervated or controlled by the nerve of interest. A suitable monitoring electrode is disclosed in U.S. Pat. No. 5,161,533 (to Richard L. Prass et al.), the entire disclosure of which is incorporated herein by reference.

One method of nerve localization involves the application of electrical stimulation near the area where the subject nerve is believed to be located. If the stimulation probe contacts or is reasonably near the nerve, the stimulation signal applied to the nerve is transmitted through the nerve to excite the related muscle. Excitement of the muscle causes an electrical impulse to be generated within the muscle; the impulse is transferred to the recording electrodes, thereby providing an indication to the surgeon as to the location of the nerve. Stimulation is accomplished using hand held monopolar or bipolar probes such as the Electrical Stimulus Probe disclosed in U.S. Pat. No. 4,892,105 (to Richard L. Prass), the entire disclosure of which is incorporated herein by reference. The probe of Pat. No. 4,892,105 has become known as the Prass Flush-Tip Monopolar Probe and is insulated up to the distal tip to minimize current shunting through undesired paths. An improved structure for a bipolar probe is disclosed in the provisional patent application entitled Bipolar Electrical Stimulus Probe (filed Aug. 12, 1998, application No. 60/096,243), the entire disclosure of which is also incorporated herein by reference.

Another method of nerve localization involves mechanical stimulation of the nerve of interest by various dissecting instruments. Direct physical manipulation of a motor nerve may cause the nerve to conduct a nerve impulse to its associated musculature. If those muscles are being monitored using a nerve integrity monitoring instrument, the surgeon will hear an acoustic representation of the muscle response in close temporal relationship to the antecedent mechanical stimulation. This will allow the nerve of interest to be roughly localized at the contact surface of the dissecting instrument.

Prior art nerve integrity monitoring instruments (such as the Xomed® NIM-2® XL Nerve Integrity Monitor, manufactured by the assignee of the present invention) have proven to be effective for performing the basic functions associated with nerve integrity monitoring such as recording EMG activity from muscles innervated by an affected nerve and alerting a surgeon when the affected nerve is activated by application of a stimulus signal, but have significant limitations for some surgical applications and in some operating room environments.

A first problem is users have noticed certain EMG measurement artifacts have a disruptive effect on monitoring and tend to cause undesirable false alarms. In particular, EMG monitoring often is performed during electrocautery in a surgical procedure, wherein powerful currents surge through and cauterize the tissue, often to devastating effect on the monitor's sensitive amplifier circuits. Electrocautery can also induce an undesired direct current (DC) offset from buildup of charge on the monitoring or sensing electrodes or within recording amplifier circuitry. A method of muting during periods of electrocautery using in-line detection of electrocautery, based upon frequency and amplitude was disclosed in Prass, et al.: "Acoustic (Loudspeaker) Facial Electromyographic Monitoring: Evoked Electromyographic Activity", Neurosurgery 19: 392–400, 1986; and an improved method involving an inductive probe pickup was described in U.S. Pat. No. 4,934,377, entitled "Intraoperative Neuroelectro-physiological Monitoring System", by Prass, et al., the entire disclosures of which are incorporated herein by reference.

Brief pop noise in the form of high frequency bursts (caused by spurious electromagnetic and current artifacts or when non-insulated metal instruments are accidentally brought into physical contact) may be recorded during nerve integrity monitoring. These brief artifacts may be confused for true electromyographic (muscle) responses and may lead to misinterpretation and false alarms, thereby reducing user confidence and satisfaction in nerve integrity monitoring. Maintenance of high common-mode rejection characteristics in the signal conditioning path has helped to reduce such interference, however, false alarms still occur. Any solution tending to eliminate or minimize false alarm problems would increase the accuracy and effectiveness of monitoring procedures.

Prior art nerve integrity monitoring devices incorporate a simple threshold detection method to identify significant electrical events based upon the amplitude of the signal voltage observed in the monitoring electrodes, relative to a baseline of electrical silence, a methodology having disadvantages for intraoperative nerve integrity monitoring. Use of intramuscular electrodes in close bipolar arrangement (as described in U.S. Pat. No. 5,161,533, cited above) provides adequate spatial selectivity and maintenance of high common mode rejection characteristics in the signal conditioning pathway for reduced interference by electromagnetic artifacts, but yield a compressed dynamic range of electrical voltage observed between the paired electrodes. When physically situated near one of the electrodes, a single nerve motor unit (e.g., activation of a single nerve fiber) may cause an adequate voltage deflection to be heard (by a surgeon listening to the EMG audio signal feedback) as a clear signal spike or exceeding a predetermined voltage threshold. Moreover, with close electrode spacing and bipolar amplification, recording of larger responses is frequently associated with internal signal cancellation, significantly reducing the amplitude of the observed electrical signal. The resultant compressed dynamic range is advantageous for supplying direct or raw EMG audio signal feedback to the operating surgeon, in that both large and small signal events may be clearly and comfortably heard at one volume setting, but an EMG audio signal feedback having compressed dynamic range provides limited ability to fractionate responses based upon magnitude of the response or obtain an accurate measure of signal power. Another disadvantage of prior art methodology of threshold detection is that the surgeon cannot readily distinguish or select between electrical artifacts and EMG activity.

A second problem is that the nerves of interest may frequently exhibit a variable amount of irritability during the surgical procedure, which may be caused by a disease process or by surgical manipulations such as mild traction or by drying or thermal effects. Such nerve irritability is recorded by nerve integrity monitoring electrodes and is displayed and annunciated to the operating surgeon as a series of "beeps" caused by repetitive triggering of threshold detection or by repetitive electromyographic spikes. Because nerve irritability does not appear in close temporal relationship to particular surgical manipulations, it provides no localizing information. When such repetitive activity is observed, the surgeon usually ceases all ongoing surgical manipulations and may irrigate the surgical field in an attempt to reduce nerve irritability. Once a reasonable effort to reduce nerve irritability has been carried out, any residual nerve irritability becomes "noise" and may interfere with the ability to detect electrically and mechanically stimulated nerve activity. Any methods to reduce the effect of background nerve irritability on detection of brief bursts of nerve activity would enhance localization of nerves of interest during periods of increased nerve irritability.

A third problem arises when monopolar probes, bipolar probes or electrified instruments are selected for electrical stimulation during intraoperative neurophysiological monitoring. Each type of probe has its own advantages, disadvantages and "best application" during intraoperative procedures. Because of a variable tendency for current shunting, the optimum stimulus intensity may vary significantly among probes. For a given probe type, the ideal stimulus intensity is low enough to allow spatial selectivity, but high enough to avoid false-negative stimulation as a result of current-shunting or other influences. The commercial EMG-type nerve monitors of the prior art have a single current-source terminating in either one or two outputs. If there are two outputs, the outputs are connected in parallel with a single common stimulus intensity setting and so there is no ability to provide separate (optimized) stimulus intensities or to guard against parallel communication between the two outputs. If both outputs are connected to stimulus instruments, undetected current-leak could occur through parallel channels and result in false-negative stimulation. At least one manufacturer or prior art monitoring instruments offers a switchable connector at the stimulus probe terminus, allowing more than one stimulus instrument to be kept in readiness, and avoiding parallel connections to the unused instruments, but performing the act of switching requires a surgical staff member such as a nurse or technician and so is cumbersome and, being time consuming, expensive.

A related problem is that prolonged nerve irritability may be due to light anesthesia, rather than to inherent nerve irritability. Any method to distinguish these two possibilities would enhance interpretation during nerve integrity monitoring.

Another problem confronting users of prior art nerve integrity monitoring devices is that quantative measurements of nerve function are relatively cumbersome to obtain, since equipment setting changes must be performed by operating room personnel while electrical stimulation procedures are performed by the operating surgeon. For example, a threshold determination for electrical nerve stimulation is an accepted indication of functional nerve integrity. Determination of response threshold requires stimulation at multiple stimulus intensities, which must be changed manually, and nerve responses must be recorded at each stimulus intensity level. With prior art technology, this process is time-intensive and discourages serial determinations during the operation as an ongoing measure of nerve integrity. Threshold determinations are typically performed only at the end of the operative procedure as a prediction of immediate postoperative function. When using prior art methods, if the threshold is found to be abnormal, the surgeon is usually unaware of when the change to abnormality occurred during the operative procedure. Any method making quantitative measurements of nerve function convenient and rapid to obtain would enhance nerve integrity monitoring.

Another concern is how functions are controlled. There is a relatively strong conceptual separation between off-line control (performed at some time other than during the procedure) and on-line control (performed during a surgical procedure), as pertains to control of intraoperative neurophysiological monitoring system functions through the use of input devices. "Off-line" operations are performed when monitoring is not actively being performed, for example, as when logging-in patient information, setting system preferences or retrieving saved-data for "post-production" analysis, whereas "on-line" refers to periods of active intraoperative neurophysiological monitoring.

In prior art nerve integrity monitoring devices, controls for off-line functions consist of front panel knobs and switches or keyboard and mouse with proprietary software to perform common setup functions and parameter adjustments. Additional back panel switches may be available to adjust less commonly changed parameters, such as stimulus rate and duration. For multi-channel nerve integrity monitoring with qualitative and quantitative signal analysis, front and back panel hardware is cumbersome and too limited in scope. Greater flexibility and convenience in off-line controls is available through use of keyboard and mouse input and software capabilities to modify and store setup information in archival files for facilitation of off-line setup functions. A limitation of prior art strategies is that the setup information is held in volatile memory during actual monitoring operations, rendering the setup information vulnerable to strong electrical surges, electromagnetic noise or accidental power interruptions. An electrical surge or accidental unplugging may cause loss of all new (different from "default") setup information, requiring a "reboot" of the system and adjustment to get back to the desired settings. Any method for off-line control allowing similar flexibility a to keyboard and mouse input and having the convenience of designated software with archival (file) storage of setup information, but without risk of erasure by spurious electrical events or accidental equipment unplugging, would represent a significant advance for nerve integrity monitoring. Stimulation devices of the prior art for neurophysiological monitoring are manually controlled through front panel potentiometers and switches or with mouse and keyboard to produce paired or burst stimuli and stimuli of opposite polarity in an alternating pattern, but lack the ability to deliver consecutive stimuli of differing intensities or alter the pattern of stimulation at a predetermined time without that time consuming manual input. Analogously, none of the monitoring instruments of the prior art provide delivery of selected stimuli in coordination with data acquisition, analysis, display, and storage. Moreover, in prior art nerve integrity devices, control of on-line functions is performed by keyboard and mouse or by front panel controls and, because of a possible breach of sterility, the operating surgeon cannot perform such functions by himself or herself and so changing equipment settings requires involvement of hospital personnel at the request of the operating surgeon and may be time-consuming, cumbersome and possibly risky, since the changed settings may be inaccurate. Any method allowing rapid and accurate changes in equipment function without the need of ancillary operating room personnel and without risk to maintenance of sterility would be considered an enhancement of nerve integrity monitoring.

An important function of intraoperative neurophysiological monitoring is detecting brief episodes of EMG activity, caused by direct electrical and mechanical stimulation. Detection allows the surgeon to localize a nerve of interest approximately at the contact surface of the dissecting or stimulating instrument. Detection of brief, localizing EMG activity is frequently obscured by the presence of repetitive EMG activity caused by "baseline" nerve irritability. Such irritability may be due to nerve compromise caused by the disease process itself or to various surgical manipulations, such as mild traction, drying, thermal stimulation, or chemical irritation. When significant repetitive activity is observed, the surgeon typically ceases all surgical manipulations and may irrigate the wound in an attempt to "quiet" nerve irritability. Once a reasonable attempt has been made to allow the nerve to become quieted, any remaining repetitive activity is essentially "noise" and may interfere with hearing more important brief EMG responses that allow localization of the nerve of interest. Such background irritability is particularly a problem during acoustic neuroma resections, which is one of the most common procedures for which facial nerve monitoring is used.

Redundancy afforded by multi-channel monitoring of (single) nerves of interest provides some opportunity to maximize the ability to detect localizing information during periods of problematic repetitive (non-localizing) activity. The most common application of nerve integrity monitoring involves monitoring the facial nerve. The facial nerve has a long course, beginning in the cranial cavity, then through a bony channel (fallopian canal) within the temporal (ear) bone, exiting behind the ear to swing forward and innervate the nerves of the facial expression. The nerve is at risk during a number of surgical procedures involving the ear, the temporal bone and intracranially. Intracranially, and in its course through the temporal bone, the nerve appears as a single nerve bundle, with no internal topographical organization. As the nerve exits the temporal bone behind the ear it finally separates into two major trunks, which further divide into 5 major branches. Multi-channel nerve integrity monitoring of the facial nerve involves placing electrodes into multiple facial muscles, representing multiple branches of the nerve. While not necessarily the preferred approach, the lack of topographical organization of the intracranial and intratemporal portions of the facial nerve, allows monitoring during removal of acoustic neuromas and during ear surgery with only one or two electromyographic channels.

Multichannel monitoring of the facial nerve is preferred in order to increase sensitivity and to provide redundancy in the event of electrode failure. Redundant facial nerve monitoring channels also provides flexibility to maximize the ability to detect localizing, brief non-repetitive EMG activity. The upper and lower facial musculature have been observed to have differential tendencies to exhibit mechanically evoked EMG activity. The lower face tends to be more sensitive in eliciting mechanically-stimulated EMG activity but also has a greater tendency to exhibit "background" nerve irritability. During periods when background repetitive EMG activity obscures auditory detection of more important and localizing non-repetitive activity, the most active EMG channels can be deleted (muted) from the signal directed to the surgeon through audio loudspeaker(s). The remaining EMG channels, having less competing background noise to interfere, are more easily heard by the operating surgeon in order to detect (localizing) mechanically and electrically stimulated EMG activity.

The majority of prior art nerve integrity monitoring devices have only two channels, which allows little redundancy and flexibility. When repetitive activity becomes bothersome and persistent, despite reasonable efforts on the part of the operating surgeon to allow the nerve to quiet down, the surgeon may ask an operating room employee to "turn the monitor down." This solution is problematic, because it may cause the surgeon to miss hearing important localizing EMG information. Alternatively, with the availability of multiple (redundant) EMG channels, a nurse or operating room technician may individually eliminate each electrode channel in an attempt to identify the offending channels, so that they may be (temporarily) eliminated. This process may be greatly facilitated, if there is some visual indication of relative EMG activity among the various EMG channels. However, even with visual displays, the process may still be time consuming and, therefore, expensive. Moreover, once certain "offending" channels have been muted, there may be long periods before the surgeon, the nurse, or operating room technician remember or "feel safe" to add these channels back to the audio signal. This may cause unnecessarily long periods of decreased sensitivity.

There is a need, then, for a nerve integrity monitoring instrument having greater flexibility and stability in use, greater sensitivity and specificity (e.g., noise rejection and artifact identification), and a user interface more readily adapted to performing the monitoring procedures required without distraction to the surgeon while concentrating on the medical aspects of the surgical procedure.

SUMMARY OF THE INVENTION

In accordance with the present invention, an intraoperative neurophysiological monitoring system includes a number of novel features, including: a digitally controlled stimulator having multiple independent stimulus outputs; an artifact detection electrode with modified wire leads to enhance its sensitivity for recording electrical artifacts; a novel method and algorithm for detecting brief artifacts using the artifact detection electrode and an enhanced method and algorithm for threshold detection; a method and algorithm for controlling the sequence of monitoring events controlled by detection of probe contact with tissue; and a method and algorithm for controlling operation of the nerve integrity monitoring system in which the electrical stimulus probe is used as a computer pointing or input device.

The intraoperative neurophysiological monitoring system stimulator preferably includes a nerve integrity monitoring instrument having multiple independent stimulus outputs to provide optimal preset stimulus output parameters for more than one probe type, thereby allowing all probes to be connected at the beginning of the case and used as needed, without delay or confusion related to switching and intensity setting changes. Independent, electrically isolated outputs also eliminate parallel connections among stimulus probes and possible current leakage between probes. An optimum number of stimulus outputs is preferably in the range of two to four. In an exemplary embodiment, three stimulus outputs include a monopolar probe, a bipolar probe and an electrified instrument, all three simultaneously connected.

For the purposes of nerve integrity monitoring, an electrical stimulus probe is used for locating and defining the contour of the nerve of interest. During such "mapping" procedures, the stimulus probe is moved about the surgical field or along the nerve contour in small controlled steps, during which the stimulus probe is in continuous contact with tissue, usually for less than one or two seconds. Alternatively, during quantitative measurements of nerve function, the stimulus probe may be applied to the nerve continuously for a few or several seconds allowing capture of electromyographic activity for analysis. Thus, if the stimulus probe is in contact with tissue for less than one or two seconds, it may be taken that the surgeon is simply locating or mapping the contour of the nerve of interest. If continuous tissue contact exceeds one or two seconds, the surgeon's intent is likely to be otherwise, such as for quantitative measurements. Further, if the stimulus probe is tapped twice or three times onto patient tissue, the temporal pattern of continuous tissue contact is quite different from either of the previous patterns and might be considered as a "request" by the surgeon.

The present invention incorporates a method of controlling a variety of nerve integrity monitoring functions through detection of the duration of continuous contact of a designated stimulus probe with patient tissue. Alternative methods to more accurately detect the temporal pattern of continuous contact of the stimulus probe with patient tissue include continuous measurement of stimulation circuit impedance and measurement of current flow using a continuous, distinct (second) subthreshold current, delivered "downstream" from the actual electrical stimulus. Continuous measurement of stimulation circuit impedance is the preferred method and provides the following benefits:

1. A quality check of the stimulus probe and circuit. Flush tip probes (e.g., as described in U.S. Pat. No. 4,892,105 and provisional patent application No. 60/096,243, filed Aug. 12, 1998, the entire disclosures of which are incorporated herein by reference) have a characteristic impedance, based partly on the cross-sectional area of the conductor. A measured characteristic impedance that is significantly below the expected characteristic impedance is sensed and indicates a parallel current path or a breach of insulation.

2. Indication of tissue contact with stimulus probe. Detection of tissue contact is used to drive a preset sequence of events, as discussed in greater detail, below.

3. A definitive solution for minimizing stimulus-pulse-related recording artifacts on other equipment by permitting current to flow only during tissue contact with a stimulus probe. Detection of a characteristic impedance decrease in the stimulus circuit during tissue contact with the stimulus probe is sensed and, in response, a relay switch is activated, allowing current flow to the appropriate probe. If a single current source is used to drive multiple stimulus outputs, detection of a characteristic impedance decrease at a stimulus probe output triggers driving relay switches to "open circuit" other stimulus probe circuits in order to definitively eliminate parallel connections with other outputs.

4. While controversial, constant voltage has been cited as more advantageous than constant current for purposes of electrical stimulation, as a means to reduce the occurrence of false-negative stimulation in the setting of stimulus shunting (Moller A, Janotta J.: Preservation of facial function during removal of acoustic neuromas: use of monopolar constant voltage stimulation and EMG. J. Neurosurg 61: 757–60, 1984). Since stimulus current is the aspect relating to stimulus adequacy and injury potential, most applications incorporate constant current stimulus sources for greater accuracy and safety in stimulus delivery. Continuous measurement of stimulus circuit impedance allows a "best of both worlds" opportunity. Stimulus probes and electrified instruments have characteristic or optimal impedance values based upon the contact surface of the particular instrument. A reduction of impedance below that of the characteristic value is taken as an indication of stimulus shunting, presumably away from the area intended for electrical stimulation. This is particularly apt to occur with use of electrified instruments, where the insulation is not carried all the way to the tip so as to not interfere with its surgical use. In combination with digital control of stimulus parameters, detection of a stimulus circuit impedance decrease below the pre-determined "optimal" value is used to trigger a compensatory increase in delivered stimulus current in a pre-determined fashion. The rate of change or slope of current increase, relative to the amount or percentage of impedance decrease, is preselected for aggressive or less aggressive compensation patterns and an upper limit of current increase is also predetermined for safety considerations. Such a compensatory current increase is safer and more reliable than simple use of constant voltage.

5. The impedance detection circuit provides a mechanism enabling use of the stimulator probe as an input device.

Additional circuitry is required for impedance detection, with an additional patient connection electrode having its own isolation, and an additional continuous, subthreshold probe signal (i.e., below the threshold required for nerve activation) must be delivered through the probe tip for measurement by the impedance detection circuit.

In an alternative embodiment, a continuous, second subthreshold current is delivered to the stimulus probe, downstream from the pulsed current used for actual nerve stimulation. Detection of flow of the continuous current provides more accurate detection of tissue contact than for pulsed stimulation alone and permits detecting a "tapping" pattern of the stimulus probe. Continuous current flow detection does not provide as many possible benefits as continuous stimulus circuit impedance measurement, but also does not require placement of an additional patient electrode and the necessary isolation circuitry.

In addition to detecting and responding to a temporal pattern of continuous tissue contact of the stimulus probe, the present stimulator is adapted for digital control. Stimulus intensity, pulse duration, and temporal pattern of stimuli presentation are controlled through a digital controller having an interface circuit. The interface stores pre-programmed stimulus algorithms or paradigms, preferably in non-volatile memory. The stimulus paradigms are preferably constructed off-line using appropriate stimulus control algorithm development software and is preferably loaded or burned into a non-volatile Read Only Memory (ROM) chip, included within the interface. During a monitoring procedure, contact with tissue will trigger a predefined sequence of events called, for purposes of nomenclature, a Tissue Contact Initiated (TCI)-Timeline, thereby activating the stored stimulus paradigms in a pre-programmed manner.

Front panel controls consist of basic stimulus intensity controls. Stimulus, pulse duration and pulse repetition rate are preferably adjusted in a limited manner by recessed DIP-switches or other user-accessed, but less prominent controls. The remaining stimulator controls are actuated through a CPU interface, such as via a PCI bus. As discussed above, monitoring parameters and complex stimulus paradigms are stored via non-volatile, programmable memory (e.g., flash memory, EEPROM). The digitally controlled stimulator executing the TCI event-sequencing time line also communicates with a CPU based data storage and analysis apparatus to direct binning of responses and to trigger archival data storage, analysis and display paradigms.

In addition to an indication of which stimulator is active and whether adequate current delivery is achieved, there is preferably also an additional indicator annunciating detection of an adequate target impedance, thereby providing a rough quality check of the stimulus probe and the entire stimulator circuit. This type of diagnostic would be best applied to the flush tip stimulus probe designs (as in U.S. Pat. No. 4,892,105), where the impedance is typically related to the cross-sectional area of the conductor contact surface.

The controller software used in monitoring the stimulus probe impedance detection circuit (or current flow detection circuit) includes an algorithm for identifying a pattern of changing impedance (or current flow change) caused by double or triple taps of the stimulator against patient tissue. When double or triple tap patterns are detected, signals are sent to the circuitry in the CPU digital interface for triggering predetermined manipulations. These command signals are preferably rendered "context sensitive" by their temporal occurrence in relation to the TCI-Time line.

Turning now to another aspect of the monitoring system of the present invention, a method is provided for detection and identification of artifacts as an aid to interpretation. For the purposes of this description, "intelligent" refers to electrode sites involving important "monitored" muscles, supplied or enervated by a particular nerve of interest. Non-intelligent refers to other electrode sites within or outside of muscles, not supplied by the nerve of interest. Current artifacts and electromagnetic field noise may best be detected by a specially constructed electrode that is inserted proximate to the recording field, but not in the (intelligent) muscles supplied by the nerve being monitored. Electrical events, simultaneously recorded in both "intelligent" electrodes (placed in muscles supplied by the nerve being monitored) and a "non-intelligent" artifact detection electrode, may be unambiguously interpreted as electrical artifacts. If the artifact detection electrode is placed in a nearby (non-intelligent) muscle not supplied by the nerve being monitored, it may also serve to detect light anesthesia. If repetitive EMG activity is simultaneously observed in monitored muscles and other muscles, it may be interpreted that the patient is beginning to wake up from anesthesia. The anesthesiologist may use this information to maintain adequate levels of anesthesia throughout the procedure. The operating surgeon may also be reassured that the observed nerve irritability is not related to surgical manipulations. The artifact detection strategy involves the construction of an artifact-detection electrode, preferably the electrode of the present invention is a modification of the electrode design of U.S. Pat. No. 5,161,533 (as discussed above). The modification provides a greater impedance imbalance between the two electrode leads, thereby reliably enhancing the antenna-like qualities of the probe and the susceptibility for detecting current and electromagnetic artifacts occurring in the immediate proximity of multiple standard electrodes placed in muscles supplied by the nerve of interest.

The artifact detection electrode of the present invention has an active-portion that is similar to the paired, bipolar Teflon coated needle electrodes, but differs in that the area of un-insulated needle is dimensioned and/or made of a suitable material to provide a reliably detectable impedance imbalance.

Preferably, the wire leads are also modified such that the lead length is approximately 6 inches longer than standard length. The extra 6-inch portion is looped over the recording field to create, effectively, an antenna over the recording field. The looped portion is treated to enhance its antenna-like properties. Optionally, in combination with or instead of using differing uninsulated areas of needle insertion portion, a resistor is placed in series with one of the two electrode leads, thereby creating a readily detected impedance imbalance, the value of which may be selected (or, with a potentiometer, adjusted) to be within a range of, preferably, zero to approximately 50,000 ohms. The resistor is preferably located on the wire lead or loop, or it may be incorporated into an associated electrical connector housing or connector body. A relative disadvantage of using a single standard recording electrode for detection of electromagnetic field and current artifacts is that the single electrode may not adequately represent the electromagnetic field for multiple active recording electrodes. The loop design, needle to insulation symmetry, fixed resistor value and relative location are the physical factors determining the "antenna like" properties of the electrode design; the various features are preferably "tuned" to obtain the optimum electrode characteristics. The electrode must be spatially selective enough to avoid pick up of "intelligent" signal, but must have adequate antenna like qualities to provide EM-field and current artifact detection to represent the entire recording field.

The uninsulated portion of the electrode needles of the artifact detection electrode is placed in a proximate, "non-intelligent" muscle, not enervated or supplied by the nerve being monitored. The looped portion of the electrode lead is placed over the recording field of the intelligent electrodes and held in place, preferably with tape.

The artifact-detection electrode output is detected and an algorithm incorporating a simple artifact-recognition strategy, based upon response distribution, is employed. The signal output of the artifact detection electrode is amplified along with that of standard "intelligent" electrodes. Brief supra-threshold signal episodes (approx. <1 sec.), detected in intelligent electrodes, trigger a logic-circuit to evaluate for simultaneous signal in the artifact-detection electrode. Simultaneous detection of supra-threshold signal in the artifact-detection electrode renders an interpretation of "artifact." If no simultaneous signal is detected in the artifact-detection electrode, the episode is interpreted as EMG in the algorithm, since it is highly unlikely that two different nerves are simultaneously (mechanically or electrically) stimulated.

For repetitive EMG activity lasting from several seconds to several minutes, detection of activity among "intelligent" electrodes indicates irritability in the nerve of interest, which may be due to surgical manipulations, whereas simultaneous detection of activity in intelligent and non-intelligent electrodes are interpreted as inadequate or "light" anesthesia, because surgically-evoked repetitive-EMG activity is otherwise unlikely to occur simultaneously in two distinct muscle groups.

An example of such an artifact detection strategy is the use of a masseter muscle electrode during facial nerve monitoring. The masseter muscle is in the proximate electromagnetic field of the facial muscles, but is not enervated by the facial nerve. Brief electromagnetic and current events that are simultaneously detected in facial and masseter muscles are readily interpreted as artifacts. Further, when repetitive activity is detected in masseter and facial electrodes, it suggests that the anesthesia is getting light.

The intraoperative neurophysiological monitoring system of the present invention includes a controller circuit and software algorithms to identify and categorize artifacts based upon the observed distribution among "intelligent" and "non-intelligent" electrode sites. In one embodiment, a logic circuit receives output from threshold detection circuits related to both "intelligent" and "non intelligent" electrode sites. When a supra threshold signal is detected in one of the "intelligent" electrode sites, the circuit becomes activated to make a determination regarding whether the signal detected was likely to have been artifact or true EMG. At the time of supra threshold signal detection in one (or more) of the "intelligent" channels, the output of the "non intelligent" channel threshold detection circuit is checked for simultaneous activation (using, e.g., a logic AND gate). If there was no supra threshold activity in the "non intelligent" channel, the logic circuit produces an output signal indicating that the observed activity was "true EMG". If simultaneous supra threshold activity was detected in both the "intelligent" and "non-intelligent" channels, the logic circuit produces an output signal indicating that the observed activity was likely to have been a non-EMG artifact.

The accuracy of the present artifact-detection strategy is dependent upon the strength of the recorded signal. Weak signals that only appear in a single channel may not distribute among intelligent and non-intelligent electrodes as predictably as when multiple electrodes are activated.

If more than one "intelligent" channel (and electrode) is utilized, the logic circuit is preferably configured to allow a user selected requirement to produce an output signal indicating the identity of a supra-threshold signal as "true EMG" or "artifact" only when two or more "intelligent" channels are simultaneously activated by supra threshold signals. This will increase the accuracy of the logic circuit determinations, reduce the frequency at which the circuit gives false positive feedback, and indicate a response of greater magnitude and probable significance.

The novel artifact-detection electrode and logical strategy for distinguishing electrical artifacts and EMG signals of the present invention works with simple threshold detection involving analog voltage measurement, but simple threshold detection has significant limitations for this application. One disadvantage is that repetitive EMG activity, caused by persistent nerve irritability, impairs the ability to detect more important episodes of non-repetitive EMG activity. Repetitive activity swamps the threshold detection circuit and causes repetitive detection of supra-threshold events.

In the present embodiment, threshold detection is improved through the use of digital signal processing (DSP), whereby all recorded electrical activity is digitized and evaluated for mathematical properties. A preferred measurement for EMG activity is rectified root mean square (rRMS), which gives a greater dynamic range for EMG activity magnitude, as detected by standard electrodes (e.g., as in U.S. Pat. No. 5,161,533, discussed above). The greater dynamic range capability improves the ability to distinguish responses, based upon the magnitude of signal power. For example, while electrical artifacts and EMG responses show considerable overlap, the peak signal power of a non-repetitive (localizing) EMG activity is usually significantly higher than for a repetitive (non-localizing) EMG activity. The digitally processed rRMS data stream for each recording channel is continuously analyzed by software for peak and average power within a variable time (probe) window. The width of the probe window (or dwell) over which power is analyzed may be varied in width (duration) up to one second, which may be "tuned" to give desired fractionating tendencies. For example, if a minimum average power value is used for determining the event detection threshold, a narrow dwell time will reduce the dynamic range and improve detection of brief responses. Lengthening the dwell time will increase the dynamic range and favor selection of only larger overall responses. Alternatively, use of peak power determinations effectively neutralizes the effect of response duration, but may have the greater ability to distinguish repetitive and non-repetitive responses. Predetermined criteria for threshold detection may include minimum values for average power, peak power or both in some combination or ratio. The use of two distinct probe windows (described in Non-Provisional Patent Application No.), separated by a variable time (inter-probe interval) allows greater accuracy in distinguishing brief non-repetitive (<1.0 sec) and longer repetitive (>1.0 sec) electrical events. If the inter-probe interval is selected to be one second, DSP (rRMS) data appears, via digital scroll, in the second probe window the same as it appeared in the first window, but one second later. A software algorithm may detect a supra-threshold event in the first probe window and re-analyze it one second later in the second probe window. At the time of detection of a supra threshold event in the second window, the activity in both windows is compared. If there is no supra threshold activity in the first probe window, the activity appearing in the second window had a duration of less than one second. If supra-threshold activity occurs simultaneously in both windows, the duration of the activity observed in the second probe window is taken as equal to or greater than one second. The inter-probe interval may be varied as a means to distinguish responses greater than or less than the selected interval value. This additional strategy may further enhance the ability to discretely select which events are to be analyzed by the artifact detection logical circuit for feedback to the operating surgeon. As indicated previously, small amplitude responses, which distribute to only one recording channel, and brief (1.0 sec) repetitive EMG responses may be analyzed relatively inaccurately by the present artifact-detection strategy. During surgical procedures, single or weak responses may be of important localizing value.

Optionally, additional DSP analysis is used to help distinguish localizing non repetitive EMG activity from electrical artifacts and brief epochs of repetitive EMG activity. For example, supra-threshold electrical events can be captured into a stable buffer for DSP analysis. Additional mathematical treatment of rRMS data is employed for acquisition of additional features which are distinct from those selected for general threshold detection purposes. Repetitive EMG activity typically exhibits a more even power distribution than non-repetitive EMG activity. A comparison or ratio of peak and average power distinguishes the two activities. The values of peak and average power required to achieve a reliable fractionation are altered within the software and different initial mathematical treatment of DSP data, such as fast Fourier transform, may be useful in separating artifacts and EMG. However, additional DSP methods are presently considered to be less reliable than the use of "intelligent" and "non-intelligent" distributions for distinguishing artifacts and EMG activity. Their use is preferably user enabled and software algorithms are capable of periodic updates in order to take advantage of the accumulation of empirical data.

In one embodiment, the output of an additional DSP analysis is available as an additional input to the logic circuit, involved with detecting "intelligent" and "non-intelligent" distributions of supra threshold events. Alternatively, outputs of the logic circuit and the additional DSP may provide input to a separate (third) controller, containing software algorithms for decision making. In either case, the software algorithms may incorporate a hierarchy or system of assigning emphasis or "weight" to various inputs. For example, if electrical activity is detected simultaneously in the artifact detection electrode with a supra-threshold event detected in an "non-intelligent" location, this input suggests that the supra-threshold event was an artifact and may override any other DSP input to the contrary. Alternatively, if there was no simultaneous activity seen in the non-intelligent electrode, but a supra-threshold event is observed in only one of three or four active "intelligent" channels, the confidence that this is a true EMG response may be considerably less assured. In such an instance, a hierarchy may be constructed within the decision making software algorithm that may allow certain DSP data to override the initial "verdict," based upon spatial distribution.

Turning to another aspect of the present invention, as noted above, quantitative measurements of nerve function in intraoperative monitoring are relatively cumbersome and require involvement of technical personnel to change stimulator settings and various recording parameters in order to acquire, analyze, display and store data. The applicant has noted that there are not many types of quantitative measurements regarding nerve function assessment, however, and that threshold and peak-amplitude measurements are the most widely used. The applicant has also discovered that paired stimuli pulses are particularly effective when assessing nerve fatigue. Operating surgeons usually have specific preferences regarding the type of quantitative data to be collected and analyzed during the course of a given surgical procedure, so there is little need for "on-the-fly" flexibility in the operating room (OR) when performing quantitative data collection.

Quantitative data on nerve function is mainly acquired through the use of an electrical stimulus probe, which provokes electromyographic responses for quantitative analysis.

The inventor has observed that surgeons use the stimulus probe differently for locating and "Mapping" than for quantitative analysis of the functional status of nerves of interest. Temporal aspects of stimulus probe use can be monitored by the tissue contact detection capability within the digital stimulator as described previously. A signal is generated in the stimulator that relates to the period of continuous contact of the stimulator probe with patient tissue. The signal continues as long as continuous tissue contact is maintained and is delivered to a system controller, which is able to initiate multiple predetermined sequential and parallel operations within the nerve integrity monitor. These operations relate to delivery of preprogrammed stimulus sequences and to the acquisition, analysis, display and archival storage of EMG data. Whether the predetermined operations are initiated or completed depends upon the duration of continuous tissue contact. For example, if the duration of continuous tissue contact is less than a preselected period of approximately one or two seconds, the controller will maintain the operational status of the nerve integrity monitor in the "search" mode. However, if the duration of continuous tissue contact exceeds the preselected time period, the stimulator or controller may alert the surgeon with an indicator tone and the controller will automatically change the operational status of the nerve integrity monitor to a quantitative assessment mode. The indicator tone may also be designed or configured to signify whether or not adequate current and/or stimulator circuit impedance has been achieved, as an indication of quality assurance.

From the time of tissue contact detection, a digital clock is initiated, controlling a preset sequence of events through a controller interface. For the purposes of this description, the period of continuous tissue contact of the stimulus probe is termed the "dwell" or "dwell time", and the series of preselected operational changes provoked by the "dwell" is termed, the "Tissue Contact Initiated Event Sequencing Time line" or "TCI-Time line". The control method to be described is designed for use with the main stimulus probe (e.g., stimulus output #1) and may be used to control all functions of the nerve integrity monitor in a preselected fashion. The described methodology need not be limited to medical applications, in that the use of any probe, where its period of dwell can be measured, may be similarly configured to control multiple functions. The following description involves the preferred embodiment, although many possible sequence strategies are available through the TCI-Time line:

Through the associated controller and controller interface, the onset of dwell will cause the artifact-detection circuit to be suspended ("defeated") throughout its duration and a preset pattern of stimulus pulses, the intensity of which is determined by front panel controls, will be delivered through the stimulator probe for locating and "mapping" the physical contour of the nerve of interest. After a preselected dwell time of approximately one second, front panel control of stimulus parameters is defeated, the pattern of stimuli is changed from single pulses to alternating paired pulses with single pulses, the intensity of which is somewhat greater (supra-maximal), and the provoked EMG responses are digitized and individually captured into stable buffers. If the dwell is interrupted before a dwell of 2 seconds, the TCI-Time line is inactivated, the artifact-detection circuit is enabled, the stable buffers are cleared of captured signal and pulsed stimuli are no longer delivered through the stimulus probe. After a 2 second preselected period of dwell, the controller and associated interface initiate a signal processing sequence, where the captured responses in stable buffers are analyzed by averaging the single and paired responses separately and computing the difference between the paired and single response by digital subtraction. The magnitude of the single and digitally subtracted responses are computed and compared. A scalar value relating to a ratio of the magnitudes of the digitally subtracted response and the single response is stored in a spreadsheet against the absolute or lapsed time (of the operation) and is displayed by CRT output automatically or upon an input "request" by the operating surgeon. The stable buffers used in these computations are automatically cleared at completion. The above computational operations occur in parallel to the following:

After a 2 second preselected period of dwell, the controller and interface defeat front panel control of stimulus parameters and alter the stimulus delivery pattern to a series of single pulses of varying intensity. The controller and interface direct the provoked EMG responses to be captured individually into stable buffers. If the dwell is interrupted prior to completion of the stimulus sequence, the TCI-Time line is discontinued, the sequence of stimulator pulses is discontinued, the stable buffers are cleared of captured signal, the artifact-detection functions are enabled and stimulus parameters are reverted to front panel controls. However, interruption of the dwell after 2 seconds does not interfere with the completion of the parallel operations described above regarding the mathematical treatment of EMG activity provoked by single and paired stimulus pulses.

If the dwell is continued (after 2 seconds), then until the stimulus sequence is completed, the stimulator or TCI-Time line controller delivers a second indicator tone and the controller and interface initiate a series of operations to generate a scalar value of response threshold. Each individually captured EMG response is analyzed for power content (peak or average), the scalar value of which is stored in a spreadsheet in conjunction with the stimulus intensity used to provoke it. The spreadsheet data relating to all stimulus intensities and corresponding responses is used to compute (or estimate) the stimulus intensity in milliamps (mA) at which half-maximal response magnitude (power) occurred. This scalar value (in mA) is then defined as the "response threshold" and is applied to a spreadsheet against absolute or lapsed time of the surgical procedure. The scalar value or a graphical plot of threshold versus operative time may be displayed automatically by CRT screen or displayed upon request by input supplied by the operating surgeon. These computational operations are carried out in parallel with progress of the dwell and may reach completion considerably after the dwell has been interrupted.

As described, the "TCI-Time line" is a multidimensional control algorithm or device utilizing information spanning both time and space. The continuous tissue contact dwell serves to initiate various series of operations through the TCI-Time line controller and interface. These operations may include simple or complex stimulus delivery paradigms, and corresponding data acquisition, analysis, display and archival storage procedures. The stimulation sequences and data handling algorithms proceed along different time lines, as per pre-programmed, parallel (processing) software algorithms. As long as the dwell continues, these operations proceed to completion in sequence. Alternatively, interruption of the dwell aborts all subsequent initiation of events along the dwell, but may allow some of the previously initiated events to reach completion as described above. The TCI-Time line controller directs operational events in different locations within the nerve integrity monitoring device. Production of stimulus pulses occurs in the stimulator portion of the monitor, while data acquisition, analysis, display and storage may occur in different locations, such as on the memory of a PCI card, CPU RAM memory or a hard drive. Thus the present TCI-Time line control system must account for multiple time dimensions and multiple locations within the monitoring device.

Detection of tissue contact is preferably achieved by continuous stimulator circuit impedance measurement or continuous measurement of current flow with use of a separate sub-threshold current delivered downstream from actual pulsed stimuli to the patient. Either of these methods will allow the detection of the temporal pattern caused by tapping the stimulator probe two or three times onto patient tissue (away from important structures) as a means of providing additional input to the controller through the tissue contact detection circuit. A "double" or "triple" tap of the stimulus probe may be preselected for altering the normal operation of the controller, such as initiating a display of previously stored data as a "time trend." That is, a "double tap" command may provoke the controller to display a time trend of a measured parameter, such as response threshold. The scalar value of stimulus intensity (mA), where the response threshold is achieved, is plotted against time (duration of the operation) to give the surgeon a clearer impression of how the nerve of interest has responded throughout the surgical procedure.

Optionally, the control capabilities of the TCI-Time line are used for analyzing and storing data derived from detection of supra threshold events. Supra threshold events may be transferred from stable buffers, described previously with regard to "additional DSP" analysis of supra threshold events, and converted to file format for archival storage. The file of the digitized signal, its scalar DSP values (e.g., peak and average rRMS), and its channel number (or identity) may be archived (as in a spreadsheet) against the absolute or lapsed (operative) time of its appearance for later (off-line) retrieval. Such capabilities improve the ability to "tune" DSP parameters for greater accuracy in detecting appropriate events for analysis, for alerting the operating surgeon and for distinguishing artifacts from true EMG.

Preferably, audio and video capture devices are integrated into the system to perform audio and video data capture functions. An independent method of distinguishing artifact and EMG supra threshold events is to interpret events in the context of the surgical procedure. If the supra threshold event occurred exactly at the time of a surgical manipulation, it may be interpreted as a mechanically stimulated (hence non-repetitive) EMG event. Alternatively, if the event appears to occur independently of surgical manipulations it is interpreted as either artifact or non-localizing (repetitive) EMG. Relatively brief (3–5 seconds) periods of digitized audio signal of the sound delivered to the surgeon through the loudspeaker in the nerve integrity monitor and digitized video of the surgical procedure, from a (microscope or hand held) camera monitoring the surgical field, is adequate to interpret the "context" of a supra threshold event. Audio and video signal may be digitized and held in FIFO "scroll" buffers within the nerve integrity monitor. For investigational purposes, the logical circuits used for detection of supra threshold events may send a signal to the TCI-Time line controller when certain preselected supra threshold events are detected; the signal provokes the TCI-Time line controller to cause the capture of digitized audio and video for an interval starting 2–4 seconds before and ending one second after the onset of the supra threshold event. The captured audio and video can then be converted to file form (*.avi, *.mpg or equivalent) and archived along with the signal data mentioned above. Such capability tremendously facilitates evaluation (validation) of various methods of event (artifact and EMG response type) detection for accuracy and effectiveness.

With the present control system, temporal aspects of stimulus probe use can be made to control an entire quantitative analysis paradigm in a pre-programmed, preset manner, based upon the needs of the user. This will involve a mix of sequential and parallel operations and smooth operation is dependent upon a seamless digital CPU interface for control of data acquisition, analysis and display, preferably in a windows based software system. The algorithm steps or command sequences and interrupt interpretations are stored on non volatile memory, such as EEPROM or "flash memory," providing fast online operation in a controller which is readily reprogrammed or modified off-line by CPU-interface. At present, the prevailing standard digital interface is the Peripheral Components Interface (PCI); it is to be understood that future developments may provide equivalents to the PCI standard. Accordingly, the following discussion is a description of but one exemplary embodiment which happens to include a PCI circuit card.

The enhanced or "complete" neurophysiological monitoring system consists of the basic monitoring unit, a processor including a CPU (e.g., an Intel Pentium® brand microprocessor) and a Peripheral Components Interface (PCI) circuit card. The CPU interfaces with the basic monitoring unit through the PCI for both off-line and on-line operations. Digitized signals from the basic monitoring unit are continually delivered (e.g., via an optical transmission link) to the PCI card, which continually routes them to temporary scroll buffers. When triggered by the tissue contact initiated (TCI) Time line or by detection of evoked EMG responses, recorded signal events are "captured," along with time, data channel identification and other relevant information. The captured signals are held in a stable buffer for DSP manipulations (e.g., Fast Fourier Transform (FFT) frequency conversion) and for conversion to a selected file format. A scroll buffer is a first-in-first-out (FIFO) image buffer storing the most recent waveform segment; the stored segment has a selected duration (e.g., approx. 2–10 seconds). A stable buffer (or bin) is also an image buffer but only holds discrete supra-threshold waveforms or events, and so effectively ignores the waveform trace between events; the stable buffer holds waveforms of selected durations or epoch lengths (e.g., approximately 1 second).

The PCI interface includes the scroll buffers and the stable buffers containing captured signal data for quantitative facial nerve signal assessment. Associated DSP circuitry is located on a PCI circuit board. There must be a relatively generous number of stable buffers (or bins) available to separately capture one or more given EMG events on multiple channels and to capture individual responses relating to stimuli of differing parameters (intensities). Additional buffer spaces or bins must also be available for digital subtraction functions, where a "third" bin stores the computed difference between two others for further quantitative analysis. The total number of bins must be adequate to handle a variety of analysis algorithms.

There must also be consideration for how signals occurring simultaneously or nearly simultaneously will be processed. The individual bin size must be adequate to store a large number of samples, thereby providing adequate waveform fidelity and the sample rate or time-base must be high enough to capture signals with the required accuracy.

The processor includes a motherboard having a CPU for acquisition of scalar data from the DSP circuits on the PCI-card and for data presentation functions such as spreadsheeting and graphing (e.g., using Lotus® or Excel® spreadsheet programs) and for controlling the display. The processor is preferably also configured to create, tag and bundle data files from the temporary stable buffers on the PCI card. Image data files are preferably bundled with corresponding "captured" audio and video files (from separate video and sound cards) and then transferred into permanent storage in appropriate locations on the processor hard drive for later review. Off-line, saved data is readily re-loaded into temporary stable buffers to permit the surgeon to review or re-analyze data to observe the effectiveness of artifact recognition and nerve function assessment.

Thus, the system delegates DSP functions to various components for rapid performance of mathematical operations and display of data. Complex stimulation paradigms are initiated by a digitally controlled stimulator, based upon temporal aspects of tissue contact by the main stimulus probe. The digital stimulator (or the controller executing the TCI-Time line algorithm) sends simultaneous signals through the PCI-interface to direct data to the appropriate buffers (or bins) for on-line analysis. Additional signals, either from the basic monitoring unit or internally generated on the PCI by pre-programmed algorithms, initiate pre-set data-display and data storage algorithms. Six to twelve different stimuli and a corresponding number of storage buffers may be employed for threshold detection. Alternating paired and single pulses will require at least three bins; one each for binning responses evoked by paired and single pulses, and a third for holding computed digital subtraction data. Optionally, within the two bins for single and paired responses or by combining the results of separate bins, repetitious responses may be used to compute a signal "average" for single and paired responses. The respective averages may be used to compute the digital subtraction data for the "third" bin.

Complete control over on-line operations of the intraoperative neurophysiological monitor of the present invention can be achieved through the use of the TCI-Time line and is preferably set up off-line using keyboard and mouse input devices through a standard personal computer operating system such as Microsoft Windows® software.

A preferred embodiment is that all changes made by off-line input procedures are transferred to the main unit of the nerve integrity monitor and "burned in" to non-volatile (EEPROM or flash) memory. As a result, the information transferred will be protected from spurious voltage spikes and accidental unplugging. This is distinct from prior art methodology, where off-line changes are stored in volatile memory, which may be susceptible to spurious voltage spikes and accidental unplugging of equipment.

Additional on-line flexibility is afforded through use of simple input devices which are convenient and easy to use, but not as comprehensive as the keyboard and mouse combination; in one embodiment, the stimulus probe is used as a pointing device for inputs to the controller. During surgery, or when "on-line", an electrical stimulus probe is preferably employed as a convenient controller input device and the TCI-Time line algorithm controls most on-line system operations, including which data are displayed to the operating surgeon on the CRT screen display. However, the surgeon may periodically want to see additional information, such as a display of a measured parameter graphed as a function of time, over course of the procedure. The stimulus probe provides a convenient and simple input device for initiating such requests, since the surgeon is likely already holding the probe, and so need not put the probe down to use a keyboard, or the like.

The TCI-Time line algorithm is triggered upon detection of tissue contact by the electrical stimulus probe. Tissue contact detection includes probe signal current flow or impedance-change detection.

In addition to providing an indication of presence or absence of tissue contact, the tissue contact detection apparatus is configured to recognize specific signatures, such as a "double tap" or "triple tap" of the stimulus probe against non-sensitive patient tissue within the surgical field. The detection of these predetermined signatures can be used to provide additional online input to the TCI-Time line controller. When such a pattern is detected, a separate signal is sent to the TCI-Time line controller for initiation of context sensitive, predetermined commands, a sequence analogous to a "double click" of a standard mouse when pointing to an icon in a Windows® compatible program. The identity of these commands are changeable, depending upon the monitoring context of the request; context is provided by the TCI-Time line algorithm. If the "double-click" occurs before the completion of a TCI-Time line controlled operation, the request is interpreted differently than for a double-click occurring after completion.

The tapping pattern can differ among different users. In order for the tapping pattern of a given user to be recognized, a setup algorithm includes an adjustment method allowing the user to input his or her individual tapping pattern. Recognition of tapping patterns may be performed by "default" recognition settings within the tissue contact detection circuitry. However, because the temporal aspects of tapping may vary significantly among individual surgeons, the preferred system allows an individual surgeon's tapping signature to be captured for later recognition. It is preferred that this is performed early in the surgical procedure, before critical stages. For this procedure, a front panel or foot pedal switch is depressed, immediately after which the surgeon performs a "double tap" or "triple tap" signature. The pattern of impedance change or current flow change detected by the tissue contact detection circuitry is stored and used as a template for recognition of similar "signature" patterns at a later time.

Also, when the double- or triple-tap input command is used, a sound sample or audible annunciation is preferably activated to indicate that the intended command has been successfully communicated. The sound sample can be any form of effective audible feedback to the user (e.g., a sound of a standard mouse double-click or triple-click).

After completion of a TCI-Time line controlled, pre-programmed stimulus sequence with corresponding quantitative data display, the algorithm preferably includes program steps for detecting a stimulus probe double-tap and, in response, displaying all similar measurements obtained from the beginning of the procedure (e.g., traced as a waveform showing voltage as a function of time), wherein a time-trend of stimulation threshold can be observed to detect a significant injury in progress. Similarly, after supra-threshold detection of an EMG response, the algorithm may include "if then" condition detection program steps wherein detection of a "double tap" is the input causing a display of the IDSP data for that response or for a display of a DSP-derived parameter, such as root mean square (RMS) power, as a function of time. Such a trend may show a loss of signal power over the course of the procedure and may indicate a fatigue trend in the nerve under observation in response to ongoing mechanical manipulations.

A simple input device used in conjunction with the TCI-Time line algorithm alternatively includes two or three button operated switches accessed from a cylindrical handle. The two button configuration may be used in a manner similar to setting of a watch; one button selects options from a menu displayed on the nerve integrity monitor and the other button is used to choose a user preference or selection from the menu of options. Alternatively, a three-button input device provides more flexibility with forward and backward movement through a menu or series of menus, since the buttons could be used to scroll up, scroll down or select an option, respectively. The simple input device is readily kept sterile in the operative field and its simplicity allows rapid data or control input and ease of use. Such a device does not require the use of the stimulating probe.

The above described simple devices for on-line use provide input through the monitoring system controller digital interface, rather than through a serial port of the host computer. Off-line operations, controlled by keyboard and mouse, preferably operate through mouse and keyboard ports on the controller CPU.

As discussed above, the intraoperative neurophysiological monitoring system also includes an enhanced method and algorithm for detecting or thresholding non-repetitive EMG events or activity (such as the short duration pulses indicative of EMG activity) as distinguished from repetitive EMG activity, even when the non-repetitive EMG events are sensed simultaneously with the repetitive EMG events, in which case the waveforms are superposed upon one another. The enhanced threshold detection algorithm includes the steps of buffering or storing a continuous series of samples of the sensed EMG waveforms from one or more sensing electrodes; the buffered waveform is processed by running the stored waveform samples serially through spaced probe first-in-first-out (fifo) sampling windows of selected duration and having a selected temporal spacing therebetween; in the preferred embodiment, the probe sampling windows have a duration in the range of 0.25 seconds to 0.5 seconds and the beginning of the first probe sampling window is temporally spaced at one second from the beginning of the second probe sampling window. The algorithm passes the stored waveform samples serially through first probe sampling window and then through the second probe sampling window. As the stored waveform samples pass through each probe sampling window, a scalar value corresponding to the rectified RMS (rRMS) power of the waveform is generated. The algorithm continuously computes a threshold value by subtracting the instantaneous value of the second probe sampling window rRMS power from the first probe sampling window rRMS power; the continuously generated results of this computation are readily plotted as a threshold value waveform. Since the algorithm passes the stored waveform samples serially through the first probe sampling window and then through the second probe sampling window, a non-repetitive EMG activity will produce a threshold value waveform having a first, positive going pulse having a width approximating the duration of the non-repetitive EMG activity (corresponding to the first probe sampling window rRMS power) and then a second negative going pulse having the same width (corresponding to the subtracted second probe sampling window rRMS power).

A repetitive EMG activity having a duration longer than the selected (1.0 second) spacing between the probe sampling windows produces a threshold value waveform having only one positive going pulse having a width approximating the duration of the interval beginning at the start of the first probe sampling window and ending at the start of the second probe sampling window (in the present example, a duration of one second). For a stored waveform having a non-repetitive EMG activity superposed on a repetitive EMG activity, as above, the algorithm will produce a threshold value waveform having a first one second long pulse including a second positive going pulse having a width approximating the duration of the non-repetitive EMG activity (corresponding to the first probe sampling window rRMS power) and then a second negative going pulse having the same width as the non-repetitive EMG activity (corresponding to the subtracted second probe sampling window rRMS power).

Whenever the enhanced threshold detection algorithm produces a threshold value waveform including a first positive going pulse followed by a second negative going pulse, there is an indication that a brief (e.g., <1.0 sec) response has occurred which may be either localizing non-repetitive EMG or artifact. Detection of such an event provokes the artifact-detection circuitry to evaluate its spatial distribution among "intelligent" and "non-intelligent" electrodes and (optionally) additional DSP algorithms in order to determine its status as an artifact or (localizing) EMG event. The surgeon is then prompted with an appropriate audible and (optionally) visual annunciation.

Another aspect of the present invention is a method for reducing irritating and distracting noise from repetitive EMG activity made possible by the enhanced threshold detection strategy described above. Data from all (and exclusively) "intelligent" EMG channels is digitized and monitored by the enhanced threshold detection circuit, employing two probe windows as described, with an inter-probe interval of approximately one second. By DSP, the average rRMS is continuously computed for both windows and the scalar value is referenced against electrical silence. With the two probe window strategy, if only one window is active at a time, the duration of a supra threshold event must be less than the inter-probe interval. If both windows are active simultaneously, the duration is equal to or greater than the inter-probe interval. Since the vast majority of non-repetitive activity is less than one second in duration, an inter-probe interval of one second is able to effectively distinguish repetitive and non-repetitive responses. Repetitive responses are detected when both probe windows are simultaneously active. In the "automatic" squelch embodiment, the scalar values of average rRMS derived from the two probe windows are continuously scanned by a software comparator constructed in non-volatile memory. The comparator is configured to compare ongoing average rRMS values against a user preselected threshold value. If the threshold value is exceeded in both probe windows, a signal is generated which activates a muting switch to eliminate that particular channel from the audio (loudspeaker) signal to the operating surgeon. If other channels reach supra threshold levels of continuous repetitive EMG activity, more channels may be muted, except the last (quietest) channel. That is, no matter how much repetitive activity, at least one "intelligent" channel is preserved for continuous audio display of EMG signals to the operating surgeon. When the average rRMS values of both windows decrease below threshold levels, the muting switch is automatically disabled.

In an alternative manual squelch embodiment, the muting function can be enabled manually. Some surgeons may prefer to decide on a "case by case" basis, when to begin muting offending EMG channels. When bothered by persistent repetitive EMG activity, the surgeon may request that a nurse or technician depress a momentary push-button switch, conveniently located on the front panel of the nerve integrity monitor. With activation of the push button switch, all (except the quietest) channels with supra threshold levels of repetitive EMG activity are muted from the audio signal to the surgeon. As with the previous "automatic" embodiment, once the activity has quieted to sub-threshold levels, the audio output is automatically re-enabled. It is preferred that the surgeon be given the option of automatic and manual operation by a simple front panel control selections.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 10 is a set of related waveform traces, plotted as a function of time, illustrating first and second probe sampling windows each of a selected duration and temporally spaced at a selected inter-probe interval.

FIG. 11 is a waveform trace, plotted with voltage as a function of time, illustrating a non-repetitive EMG activity.

FIG. 12 is a waveform trace, plotted with voltage as a function of time, illustrating a repetitive EMG activity.

FIG. 13 is a set of related waveform traces, plotted with voltage as a function of time, illustrating a non-repetitive EMG activity superposed on (or occurring and sensed simultaneously with) a repetitive EMG activity.

DESCRIPTION OF THE PREFERRED EMBODIMENT

Figure 1:
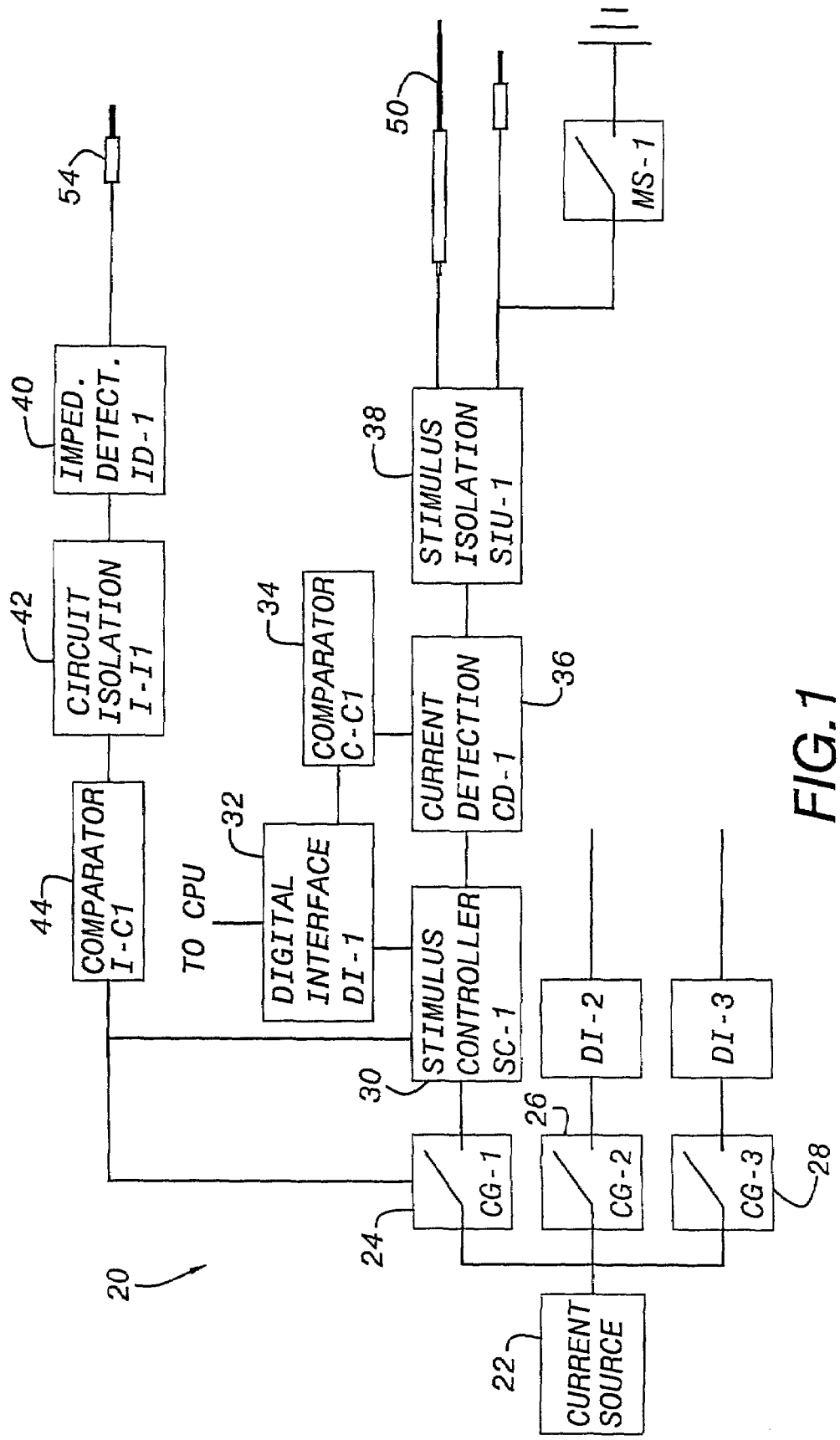
FIG. 1 is a block diagram of the intraoperative neurophysiological monitoring system digitally controlled stimulator impedance and current flow detection circuit elements, in accordance with the present invention.

Referring specifically to FIG. 1 of the accompanying drawings, an intraoperative neurophysiological monitoring system 20 includes digitally controlled stimulator impedance and current flow detection circuit elements for use during intraoperative neurophysiological monitoring and preferably in conjunction with a tissue contact initiated event sequencing time line algorithm (TCI-Time line) for control of data acquisition, analysis, display and storage. A current source 20 is connected with parallel inputs to three electronic switches ("current-gates") CG-1, CG-2, and CG-3, 24, 26 and 28; although separate current sources for each stimulus output may be employed, a single current source is shown here. Each stimulus output includes a stimulus-controller (e.g., SC-1) 30 controlling the intensity, duration and temporal patterns of delivered stimulus-pulses. The controller is, in turn, connected with controlled by and responsive to a digital-interface (e.g., DI-1) 32 which is in turn connected to a CPU (not shown) and a comparator (e.g., C-C1) 34. Each stimulus output also includes a current detection circuit (e.g., CD-1) 36 and a stimulus isolation unit (e.g., SIU-1) 38. Each stimulus output includes an electronic switch (e.g., 24) which is responsive to and driven by tissue-contact detection. The present design uses impedance-detection as the means to detect tissue contact. Switches 24, 26 and 28 are kept in the open circuit position until tissue contact is detected at one of the cathode terminals at the output. Tissue contact produces a signal from the corresponding impedance-detection circuit to close the electronic switch, the probe for which is in contact with tissue, and open circuits the other switches. Preferably, switches 24, 26 and 28 are configured so that only one switch (e.g., 24) can be closed at a time. Current flow is measured for each stimulus output by a current-flow detection circuit (e.g., 36), and the output of circuit 36 drives the digital indication or read out of current-flow for the corresponding stimulus output. The output signal of the current detection circuit 36 is responsive to measured current flow and is compared against the "user-intended" current level by comparator circuit 34.

If the current value falls within predetermined limits (90–95%), comparator circuit 34 outputs an "enable" signal, to be used to trigger an "adequate-current" speech sample or tone, thereby providing audible feedback for the surgeon. The detection of the enable signal is a triggering event for execution of the TCI-Time line algorithm in the CPU and digital interface 32. Each stimulus output includes a digital interface (e.g., 32) storing various stimulus paradigms, which are initiated in a pre-programmed fashion (as by the TCI-Time line algorithm) upon tissue-contact detection. Digital-interface 32 also directs data capture, analysis, display and storage in a pre-programmed fashion per the TCI-Time line. The interface 32 consists of two components, one of which is located in a system main monitoring unit, the other of which is located in a PCI-bus slot in a system computer. Digital interface 32 employs stimulus controller 30 which shapes the current provided from the current-source 22 into stimuli of pre-programmed intensity, duration, and having a pre-selected temporal pattern. The stimulus controller 30 is driven by digital interface 32, which stores stimulus-paradigms in non-volatile memory and initiates the stimulus paradigms as pre-programmed within the TCI-Time line algorithm. Digital interface 32 also controls functions relating to data acquisition, analysis, display, and storage through its connection with the CPU. For stimulus output #2, #3 or both, digital interface 32 may be configured to input measured values of stimulus circuit impedance and make pre-programmed adjustments of stimulus intensity, based upon impedance values. It is anticipated that stimulus output #1 will be used with a flush-tip stimulus probe for which such an application is not necessary.

In FIG. 1, impedance detection circuit ID-1, 40 is included to provide an indication of tissue-contact and to measure nominal stimulus circuit impedance. Detection of tissue-contact is used to initiate the TCI-Time line algorithm and measurement of impedance is used to provide a "quality-check" of the stimulus-circuit integrity and provide a means of adjusting stimulus intensity to the level of current shunting. For impedance measurement, impedance detection circuit 40 provides a small, sub-threshold signal that is detected. The patient connections for the impedance-detection circuit 40 is electrically or optically isolated from the line-powered circuitry by connection through circuit isolation element I-I1, 42, and is preferably connected to a comparator 44 which receives the output of impedance detection circuit 40 and computes scalar representations of measured stimulus-circuit impedance. Comparator 44 provides an output for use by the digital interface 32 to drive the various data-handling operations and preprogrammed stimulus intensity adjustments.

Figure 2:
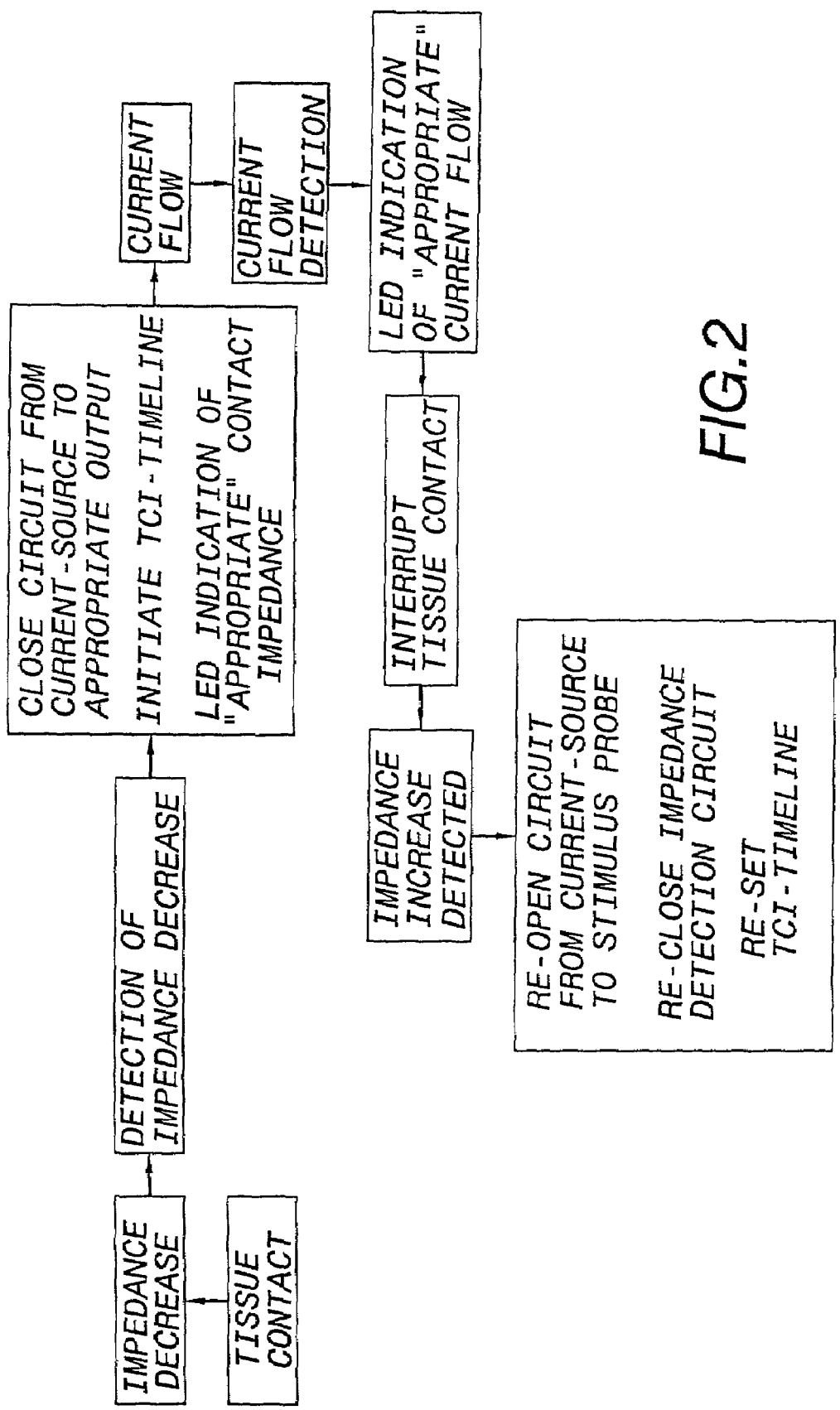
FIG. 2 is a flow diagram illustrating the impedance detection algorithm for detection of tissue contact, for use with the monitoring system stimulator impedance detection circuit of FIG. 1, in accordance with the present invention.

Turning now to FIG. 2, a flow diagram illustrates the impedance detection algorithm for detection of tissue contact, for use with the monitoring system stimulator impedance detection circuit of FIG. 1. Once probe 50 is brought into contact with the tissue of a patient, the probe impedance (which is initially an open circuit impedance at the probe tip) is reduced to the measured tissue impedance and switch 24 is closed to provide stimulus current. Substantially simultaneously, the TCI-time line algorithm is initiated and a light emitting diode (LED) is illuminated, thus providing an indication of "appropriate" tissue contact impedance. Stimulus current flows through probe 50 and the nerve tissue and the current flow is detected in current detection circuit 36; if the detected current is of the appropriate magnitude, an LED is illuminated, thus providing an indication of "appropriate" current flow. Once the surgeon lifts the probe and interrupts tissue contact, the increased, open circuit impedance is detected, and switch 24 is open circuited in response, while the impedance detection circuit 40 is activated and the TCI-Time line algorithm is reset.

Figure 3:
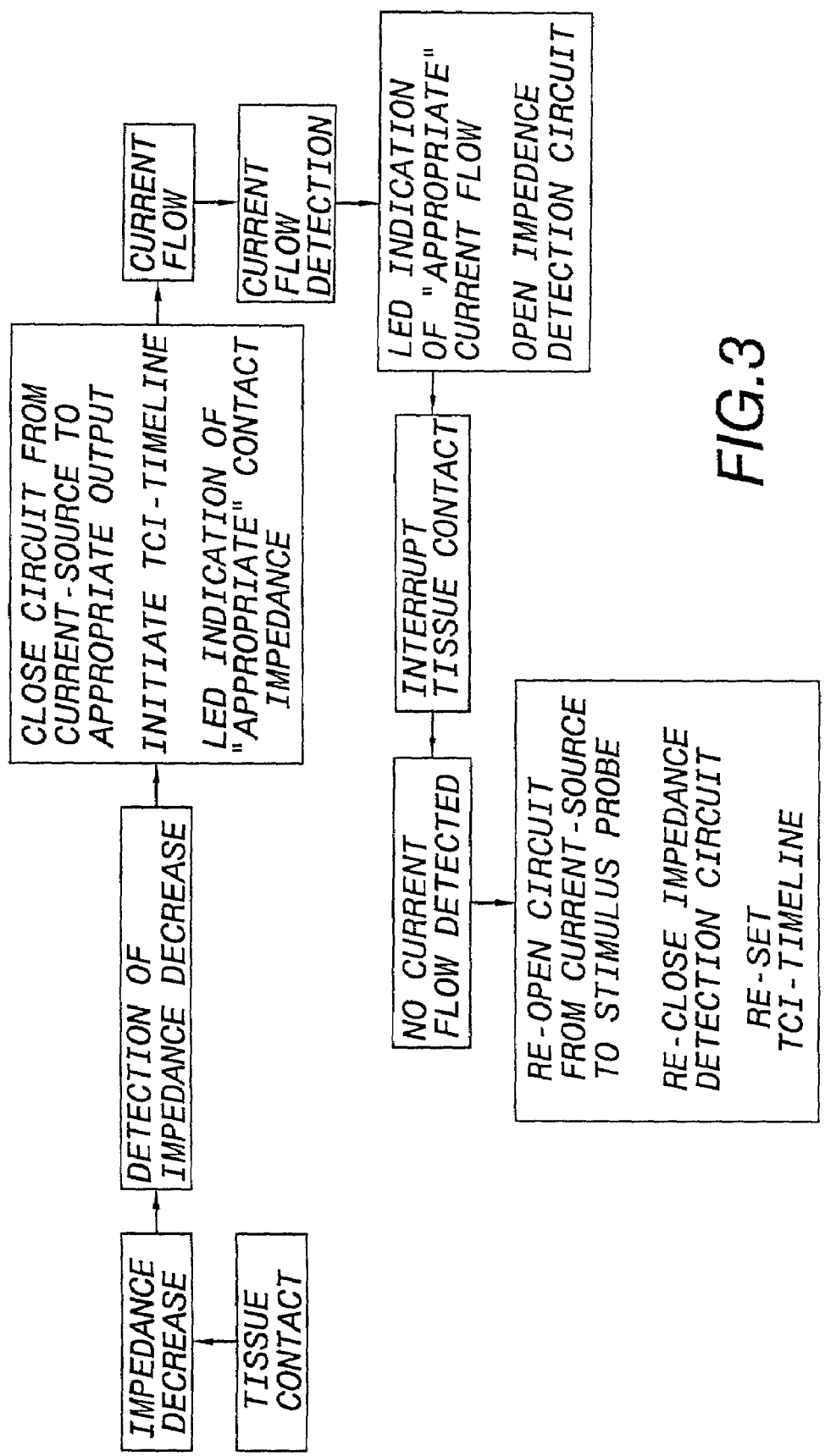
FIG. 3 is a flow diagram illustrating the impedance detection algorithm for detection of tissue contact, for use with the monitoring system stimulator current and impedance detection circuits of FIG. 1, in accordance with the present invention.

FIG. 3 is a flow diagram illustrating the impedance detection algorithm for detection of tissue contact, for use with the monitoring system stimulator current and impedance detection circuits of FIG. 1. Once probe 50 is brought into contact with the tissue of a patient, the probe impedance (which is initially an open circuit impedance at the probe tip) is reduced to the measured tissue impedance and switch 24 is closed to provide stimulus current. Substantially simultaneously, the TCI-time line algorithm is initiated and a light emitting diode (LED) is illuminated, thus providing an indication of "appropriate" tissue contact impedance. Stimulus current flows through probe 50 and the nerve tissue and the current flow is detected in current detection circuit 36; if the detected current is of the appropriate magnitude, the impedance detection circuit 40 is open circuited and an LED is illuminated, thus providing an indication of "appropriate" current flow. Once the surgeon lifts the probe and interrupts tissue contact, current flow stops and the lack of current flow is detected with current detection circuit 36, whereupon switch 24 is open circuited in response, while the impedance detection circuit 40 is re-closed and the TCI-Time line algorithm is reset.

The intraoperative neurophysiological monitoring system 20 comprises a stimulator that preferably includes a nerve integrity monitoring instrument having multiple independent stimulus outputs to provide optimal preset stimulus output parameters for more than one probe type, thereby allowing all probes to be connected at the beginning of the case and used as needed, without delay or confusion related to switching and intensity setting changes. Independent, electrically isolated outputs also eliminate parallel connections among stimulus probes and possible current leakage between probes. In the exemplary embodiment of FIG. 1, three stimulus outputs include a monopolar probe 50, a bipolar probe (not shown) and an electrified instrument (not shown), all three simultaneously connected.

For the purposes of nerve integrity monitoring, electrical stimulus probe 50 is used for locating and defining the contour of the nerve of interest. During "mapping" procedures, the stimulus probe 50 is moved about the surgical field or along the nerve contour in small controlled steps, during which probe 50 is in continuous contact with tissue, usually for less than one or two seconds. Alternatively, during quantitative measurements of nerve function, probe 50 may be applied to the nerve continuously for a few or several seconds allowing capture of electromyographic activity for analysis. Thus, if probe 50 is in contact with tissue for less than one or two seconds, it may be taken that the surgeon is simply locating or mapping the contour of the nerve of interest. If continuous tissue contact exceeds one or two seconds, the surgeon's intent is likely to be otherwise, such as for quantitative measurements. Further, if the stimulus probe 50 is tapped twice or three times onto patient tissue, the temporal pattern of continuous tissue contact is different from either of the previous patterns and is considered a "request" by the surgeon.

The present invention incorporates a method of controlling a variety of nerve integrity monitoring functions through detection of the duration of continuous contact of probe 50 with patient tissue. Alternative methods to more accurately detect the temporal pattern of continuous contact of probe 50 with patient tissue include continuous measurement of stimulation circuit impedance and measurement of current flow using a continuous, distinct (second) sub-threshold current, delivered "downstream" from the actual electrical stimulus (e.g., using the downstream current source, CS-2, as shown in FIG. 4).

Returning to FIG. 1, stimulation circuit impedance is accomplished by using the impedance detection circuit 40 to enable use of stimulator probe 50 as an input device.

Additional circuit elements 40, 42, 44 are required for impedance detection, with an additional patient connection electrode 54 (e.g., a monopolar subdermal electrode) having its own isolation circuit 42, and an additional continuous, sub-threshold probe signal (i.e., below the threshold required for nerve activation) must be delivered through the probe tip for measurement by the impedance detection circuit 42.

Figure 4:
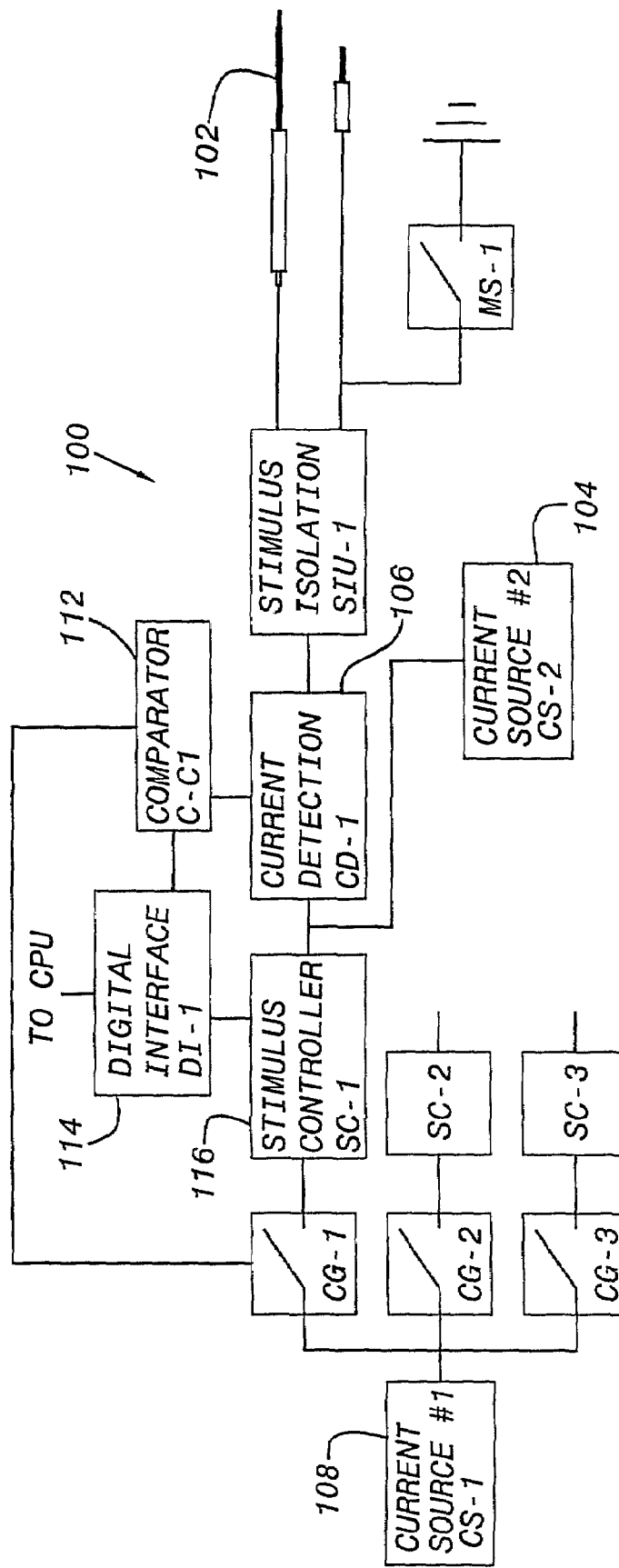
FIG. 4 is a block diagram of the intraoperative neurophysiological monitoring system digitally controlled stimulator current flow detection circuit, in accordance with the present invention.

In an alternative embodiment of the monitoring system 100 (as shown in FIG. 4), a continuous, second sub-threshold current generated in current source #2, CS-2, 104 is delivered to a stimulus probe 102, downstream from the pulsed current used for actual nerve stimulation. Detection of flow of the continuous current provides more accurate detection of tissue contact than for pulsed stimulation alone and permits detecting a "tapping" pattern of the stimulus probe. Continuous current flow detection does not provide as many possible benefits as continuous stimulus circuit impedance measurement, but also does not require placement of an additional patient electrode and the necessary isolation circuitry.

In addition to detecting and responding to a temporal pattern of continuous tissue contact of the stimulus probe, the stimulator of FIGS. 1 and 4 is adapted for digital control. Stimulus intensity, pulse duration, and temporal pattern of stimuli presentation are controlled through a digital controller having a digital interface circuit 32. The interface 32 (and the accompanying CPU) stores pre-programmed stimulus algorithms or paradigms, preferably in non-volatile memory. The stimulus paradigms are preferably constructed off-line using appropriate stimulus control algorithm development software and is preferably loaded or burned into a non-volatile Read Only Memory (ROM) chip, included within the interface. During a monitoring procedure, contact with tissue will trigger a predefined sequence of events called, for purposes of nomenclature, a Tissue Contact Initiated (TCI)-Time line, thereby activating the stored stimulus paradigms in a pre-programmed manner.

Front panel controls for monitoring system 20 consist of basic stimulus intensity controls. Stimulus, pulse duration and pulse repetition rate are preferably adjusted in a limited manner by recessed DIP-switches or other user-accessed, but less prominent controls. The remaining stimulator controls are actuated through the digital CPU interface 32, such as via a PCI bus. As discussed above, monitoring parameters and complex stimulus paradigms are stored via non-volatile, programmable memory (e.g., flash memory, EEPROM). The digitally controlled stimulator executing the TCI event-sequencing time line also communicates with a CPU (not shown) based data storage and analysis apparatus to direct binning or storing of responses and to trigger archival data storage, analysis and display paradigms.

In addition to an indication of which stimulator is active and whether adequate current delivery is achieved, there is preferably also an additional indicator annunciating detection of an adequate target impedance, thereby providing a rough quality check of the stimulus probe and the entire stimulator circuit. This type of diagnostic would be best applied to the flush tip stimulus probe designs (as in U.S. Pat. No. 4,892,105), where the impedance is typically related to the cross-sectional area of the conductor contact surface.

The controller software used in monitoring the stimulus probe impedance detection circuit 40 (or current flow detection circuit 36) includes an algorithm for identifying a pattern of changing impedance (or current flow change) caused by double or triple taps of probe 50 against patient tissue. When double or triple tap patterns are detected, signals are sent to the circuitry in the CPU digital interface 32 for triggering predetermined manipulations. These command signals are preferably rendered "context sensitive" by their temporal occurrence in relation to the TCI-Time line.

Returning now to FIG. 4, the intraoperative neurophysiological monitoring system 100 includes digitally controlled stimulator current flow detection circuit CD-1, 106 and a second, downstream current source CS-2, 104, and is well suited to performing the method of the present invention with current flow detection only. Current source 108 comprises the main source of current to provide nerve stimulation; although separate current sources for each stimulus output may be employed, a single source is shown.

Current Source #2, 104 provides continuous, sub-threshold current through the cathode of stimulus output probe 102 for detection of tissue contact. As above, the switches or current gates CG-1, CG-2 and CG-3 are actuated or driven by tissue contact detection. The present design uses current-flow detection as the means to detect tissue contact. The switches ("current-gates") are kept in the open-position until tissue contact is detected at one of the cathode terminals at the output which produces a signal from the corresponding impedance-detection circuit to close the electronic switch for the probe (e.g., 102) in contact with tissue, and opens the others. As above, the switches are configured so that only one switch can be closed at a time. Each stimulus output also has a stimulus-controller SC-1 that effects the intensity, duration and temporal patterns of delivered stimulus pulses. The controller is, in turn, controlled by a digital-interface DI-1. Current-flow will be measured for each stimulus output by a current-flow detection circuit (e.g. CD-1). Second current-source 104 injects a continuous, sub-threshold current beyond the current-gate CG-1, which is used for the detection of tissue contact. During delivery of "stimulus current" the output of the CS-2 circuit is used to drive the digital readout of current-flow for the corresponding stimulus output (e.g., probe 102).

The output of Current Flow Detector (CFD) CD-1, relating to measured "stimulus-current" flow, is compared against the "user-intended" level by a "comparator" circuit 112. If the value falls within predetermined limits (90–95%), the comparator circuit 112 puts out an "enable" signal used to trigger an "adequate-current" speech-sample or tone, and preferably also incorporated as an "enable" signal for the TCI-Time line.

Digital interface DI-1, 114 stores various stimulus-paradigms which are initiated in a pre-programmed fashion (TCI-Time line) by detection of tissue contact of the primary stimulus probe 102. Digital interface 114 also directs data capture, analysis, display and storage in a pre-programmed fashion per the TCI-Time line. Interface 114 consists of two components, one of which is located in the main unit, the other of which is located in a PCI-bus slot in the computer. The digital interface 114 controls a stimulus controller SC-1, 116 which shapes the current provided from current source 108 into stimuli of pre-programmed intensity, duration, and temporal pattern. The digital interface DI-1, 114 also controls functions relating to data acquisition, analysis, display, and storage through a connection with a CPU (not shown).

For stimulus outputs #2, #3 or both (shown only through the SC segments), the digital-interface may be configured to input measured-values of stimulus-circuit impedance and make pre-programmed adjustments of stimulus intensity, based upon measured-impedance values. It is anticipated that stimulus output #1 (shown in its entirety) will be used with a flush-tip stimulus probe 102 for which such an application is unnecessary.

Figure 5:
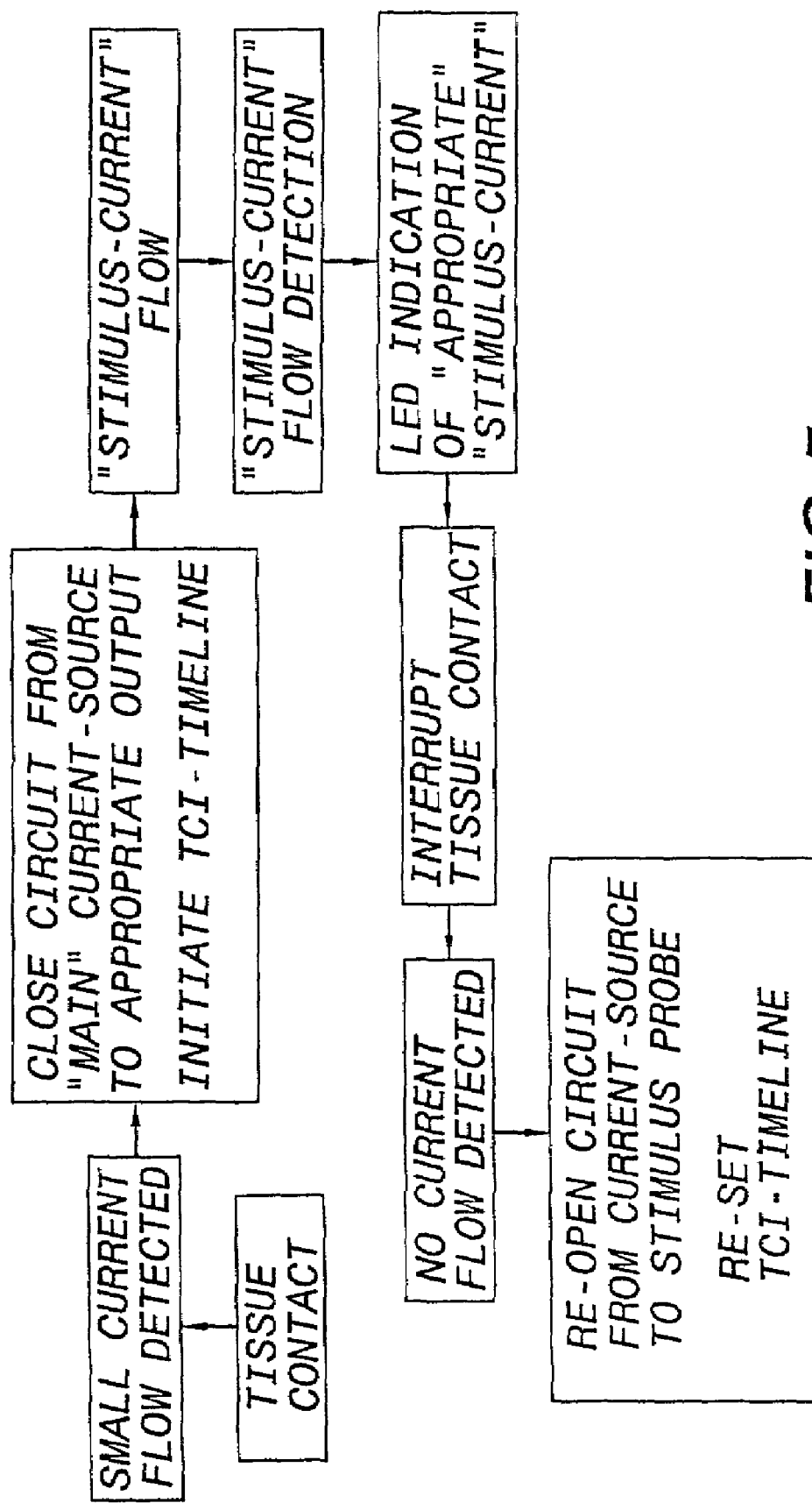
FIG. 5. is a flow diagram illustrating the current flow detection algorithm for detection of tissue contact, for use with the monitoring system stimulator current flow detection circuit of FIG. 4, in accordance with the present invention.

FIG. 5. is a flow diagram illustrating the current flow detection algorithm for detection of tissue contact, for use with the monitoring system stimulator current flow detection circuit of FIG. 4, in accordance with the present invention. Once probe 102 is brought into contact with the tissue of a patient, a small probe current from second current source 104 is sensed and current gate or switch CG-1 is closed to provide stimulus current. Substantially simultaneously, the TCI-time line algorithm is initiated and, optionally, a light emitting diode (LED) is illuminated, thus providing an indication of "appropriate" tissue contact impedance. Stimulus current flows through probe 102 and the nerve tissue and the stimulus current flow is detected in current detection circuit CD-1, 106; if the detected current is of the appropriate magnitude, an LED is illuminated, thus providing an indication of "appropriate" current flow. Once the surgeon lifts the probe and interrupts tissue contact, current flow stops and the lack of current flow is detected with current detection circuit 106, whereupon switch CG-1 is open circuited in response and the TCI-Time line algorithm is reset.

Figure 6:
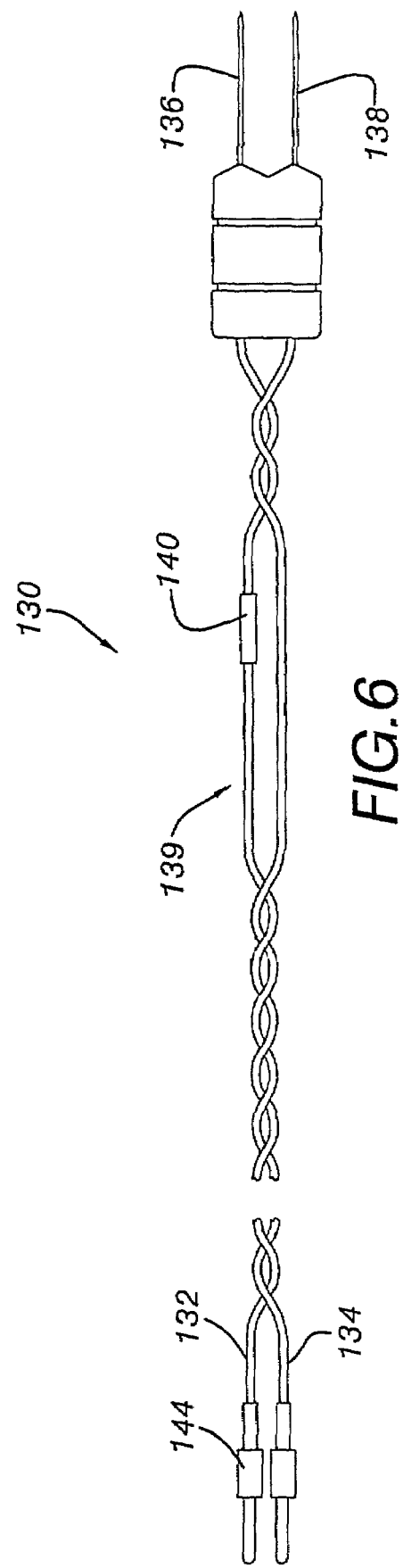
FIG. 6 is a top view of an artifact detection electrode in accordance with the present invention.

FIG. 6 is a top view of an artifact detection electrode 130 for use during intraoperative neurophysiological monitoring to provide a reliable means of detecting electromagnetic and current artifacts, occurring in the physical-proximity of multiple active recording electrodes. Signal output from artifact-detection electrode 130 is used in a simple logic paradigm for the purposes of distinguishing electromagnetic (EM) and current artifacts from biophysiological responses, and is useful to detect when general anesthesia is becoming inadequate or light. Probe 130 is well suited for detection and identification of artifacts as an aid to interpretation, and can be placed in different groups of muscles to obtain different measurements. For the purposes of this description, "intelligent" refers to electrode sites involving important "monitored" muscles, supplied or enervated by a particular nerve of interest. Non-intelligent refers to other electrode sites within or outside of muscles, not supplied by the nerve of interest. Current artifacts and electromagnetic field noise may best be detected by electrode 130 when inserted proximate to the recording field, but not in the (intelligent) muscles supplied by the nerve being monitored. Electrical events, simultaneously recorded in both "intelligent" electrodes (placed in muscles supplied by the nerve being monitored) and a "non-intelligent" artifact detection electrode, may be unambiguously interpreted as electrical artifacts. If the artifact detection electrode is placed in a nearby (non-intelligent) muscle not supplied by the nerve being monitored, it may also serve to detect light anesthesia. If repetitive EMG activity is simultaneously observed in monitored muscles and other muscles, it may be interpreted that the patient is beginning to wake up from anesthesia. The anesthesiologist may use this information to maintain adequate levels of anesthesia throughout the procedure. The operating surgeon may also be reassured that the observed nerve irritability is not related to surgical manipulations. This artifact detection strategy is abetted by the construction of artifact-detection electrode 130 which is a modification of the electrode design of U.S. Pat. No. 5,161,533 (as discussed above). The modification provides a greater impedance imbalance between the two electrode leads 132, 134, thereby reliably enhancing the antenna-like qualities of the probe and the susceptibility for detecting current and electromagnetic artifacts occurring in the immediate proximity of multiple electrodes placed in muscles supplied by the nerve of interest.

Artifact detection electrode 130 has an active-portion that is similar to the paired, bipolar Teflon coated needle electrodes, but differs in that the area of un-insulated needle 136, 138 is dimensioned and/or made of a suitable material to provide a reliably detectable impedance imbalance.

Preferably, wire leads 132, 134 are also modified such that the lead length is approximately 6 inches longer than standard length. The extra 6-inch portion is looped over the recording field to create, effectively, an antenna 139 over the recording field. The looped portion is treated to enhance its antenna-like properties. Optionally, in combination with or instead of using differing uninsulated areas of needle insertion portion, a resistor 140 is placed in series with one of the two electrode leads, thereby creating a readily detected impedance imbalance, the value of which may be selected (or, with a potentiometer, adjusted) to be within a range of, preferably, zero to approximately 50,000 ohms. Resistor 140 is preferably located on the wire lead or loop 139, or it may be incorporated into an associated electrical connector housing or connector body (e.g., 144). A relative disadvantage of using a single standard recording electrode for detection of electromagnetic field and current artifacts is that the single electrode may not adequately represent the electromagnetic field for multiple active recording electrodes. The loop design, needle to insulation symmetry, fixed resistor value and relative location are the physical factors determining the "antenna like" properties of the electrode design; the various features are preferably "tuned" to obtain the optimum electrode characteristics. The electrode must be spatially selective enough to avoid pick up of "intelligent" signal, but must have adequate antenna like qualities to provide EM-field and current artifact detection to represent the entire recording field.

The uninsulated portion of the electrode needles 136, 138 of the artifact detection electrode 130 is placed in a proximate, "non-intelligent" muscle, not enervated or supplied by the nerve being monitored. The looped portion 139 of the electrode lead is placed over the recording field of the intelligent electrodes and held in place, preferably with tape.

The artifact-detection electrode output is detected and an algorithm incorporating a simple artifact-recognition strategy, based upon response distribution, is employed. The signal output of the artifact detection electrode is amplified along with that of standard "intelligent" electrodes. Brief supra-threshold signal episodes (approx. <1 sec.), detected in intelligent electrodes, trigger a logic-circuit to evaluate for simultaneous signal in the artifact-detection electrode. Simultaneous detection of supra-threshold signal in the artifact-detection electrode renders an interpretation of "artifact." If no simultaneous signal is detected in the artifact-detection electrode, the episode is interpreted as EMG in the algorithm, since it is highly unlikely that two different nerves are simultaneously (mechanically or electrically) stimulated.

For repetitive EMG activity lasting from several seconds to several minutes, detection of activity among "intelligent" electrodes indicates irritability in the nerve of interest, which may be due to surgical manipulations, whereas simultaneous detection of activity in intelligent and non-intelligent electrodes are interpreted as inadequate or "light" anesthesia, because surgically-evoked repetitive-EMG activity is otherwise unlikely to occur simultaneously in two distinct muscle groups.

An example of such an artifact detection strategy is the use of a masseter muscle electrode during facial nerve monitoring. The masseter muscle is in the proximate electromagnetic field of the facial muscles, but is not enervated by the facial nerve. Brief electromagnetic and current events that are simultaneously detected in facial and masseter muscles are readily interpreted as artifacts. Further, when repetitive activity is detected in masseter and facial electrodes, it suggests that the anesthesia is getting light.

The intraoperative neurophysiological monitoring system of the present invention includes a controller circuit and software algorithms to identify and categorize artifacts based upon the observed distribution among "intelligent" and "non-intelligent" electrode sites. In one embodiment, a logic circuit receives output from threshold detection circuits related to both "intelligent" and "non intelligent" electrode sites. When a supra threshold signal is detected in one of the "intelligent" electrode sites, the circuit becomes activated to make a determination regarding whether the signal detected was likely to have been artifact or true EMG.

At the time of supra threshold signal detection in one (or more) of the "intelligent" channels, the output of the "non intelligent" channel threshold detection circuit is checked for simultaneous activation (using, e.g., a logic AND gate). If there was no supra threshold activity in the "non intelligent" channel, the logic circuit produces an output signal indicating that the observed activity was "true EMG". If simultaneous supra threshold activity was detected in both the "intelligent" and "non-intelligent" channels, the logic circuit produces an output signal indicating that the observed activity was likely to have been a non-EMG artifact.

The accuracy of the present artifact-detection strategy is dependent upon the strength of the recorded signal. Weak signals that only appear in a single channel may not distribute among intelligent and non-intelligent electrodes as predictably as when multiple electrodes are activated.

If more than one "intelligent" channel (and electrode) is utilized, the logic circuit is preferably configured to allow a user selected requirement to produce an output signal indicating the identity of a supra threshold signal as "true EMG" or "artifact" only when two or more "intelligent" channels are simultaneously activated by supra threshold signals. This will increase the accuracy of the logic circuit determinations, reduce the frequency at which the circuit gives false positive feedback, and indicate a response of greater magnitude and probable significance.

The novel artifact-detection electrode and logical strategy for distinguishing electrical artifacts and EMG signals of the present invention works with simple threshold detection involving analog voltage measurement, but simple threshold detection has significant limitations for this application. One disadvantage is that repetitive EMG activity, caused by persistent nerve irritability, impairs the ability to detect more important episodes of non-repetitive EMG activity. Repetitive activity swamps the threshold detection circuit and causes repetitive detection of supra threshold events.

In the present embodiment, threshold detection is improved through the use of digital signal processing (DSP), whereby all recorded electrical activity is digitized and evaluated for mathematical properties. A preferred measurement for EMG activity is rectified root mean square (rRMS), which gives a greater dynamic range for EMG activity magnitude, as detected by standard electrodes (e.g., as in U.S. Pat. No. 5,161,533, discussed above). The greater dynamic range capability improves the ability to distinguish responses, based upon the magnitude of signal power. For example, while electrical artifacts and EMG responses show considerable overlap, the peak signal power of a non-repetitive (localizing) EMG activity is usually significantly higher than for a repetitive (non-localizing) EMG activity. The digitally processed rRMS data stream for each recording channel is continuously analyzed by software for peak and average power within a variable time (probe) window. The width of the probe window (or dwell) over which power is analyzed may be varied in width (duration) up to one second, which may be "tuned" to give desired fractionating tendencies.

Another aspect of the present invention is an artifact detection method for use during intraoperative neurophysiological monitoring and preferably in conjunction with electrode 130, which is specifically-designed and used for detection of artifacts.

Additionally, the present invention involves a circuit that is specifically designed to identify artifacts based upon the observed distribution among "intelligent" and "non-intelligent" electrode sites.

A simple logic-circuit receives output from threshold detection circuits related to both "intelligent" and "non-intelligent" electrode sites. When a supra-threshold (i.e., over threshold) signal is detected in one of the "intelligent" electrode sites, the circuit becomes activated to make a determination regarding whether the signal detected was likely to have been artifact or true EMG. At the time of supra-threshold signal detection in one (or more) of the "intelligent" channels, the output of the "non-intelligent" channel threshold detection circuit is checked for simultaneous activation. If there was no supra threshold activity in the "non-intelligent" channel, the logical circuit will produce an output signal, indicating that the observed activity was likely to be true-EMG. If simultaneous supra-threshold activity was observed in the "non-intelligent" channel was detected, the logical circuit will produce an output signal, indicating that the observed activity was likely to have been artifact.

Preferably, more than one "intelligent" channel is utilized and so the logical circuit is configured to only become activated (i.e., to make a logical determination) when two or more "intelligent" channels are simultaneously activated, thereby increasing the accuracy of the logical-circuit determinations, reducing the frequency at which the circuit gives feedback, and indicating to the surgeon when there has been a more significant response.

If DSP analysis of "intelligent" signals is used for the purpose of artifact identification, the output of that separate determination may be fed into the present logical circuit. Depending upon whether or not the DSP-related determination agrees with the present distribution-related determination, the logical circuit output might generate an appropriate signal to indicate "highly-probable," "probable," "possible," or "inconclusive," depending upon the differential weighting given to the respective methods of determination.

Figure 7:
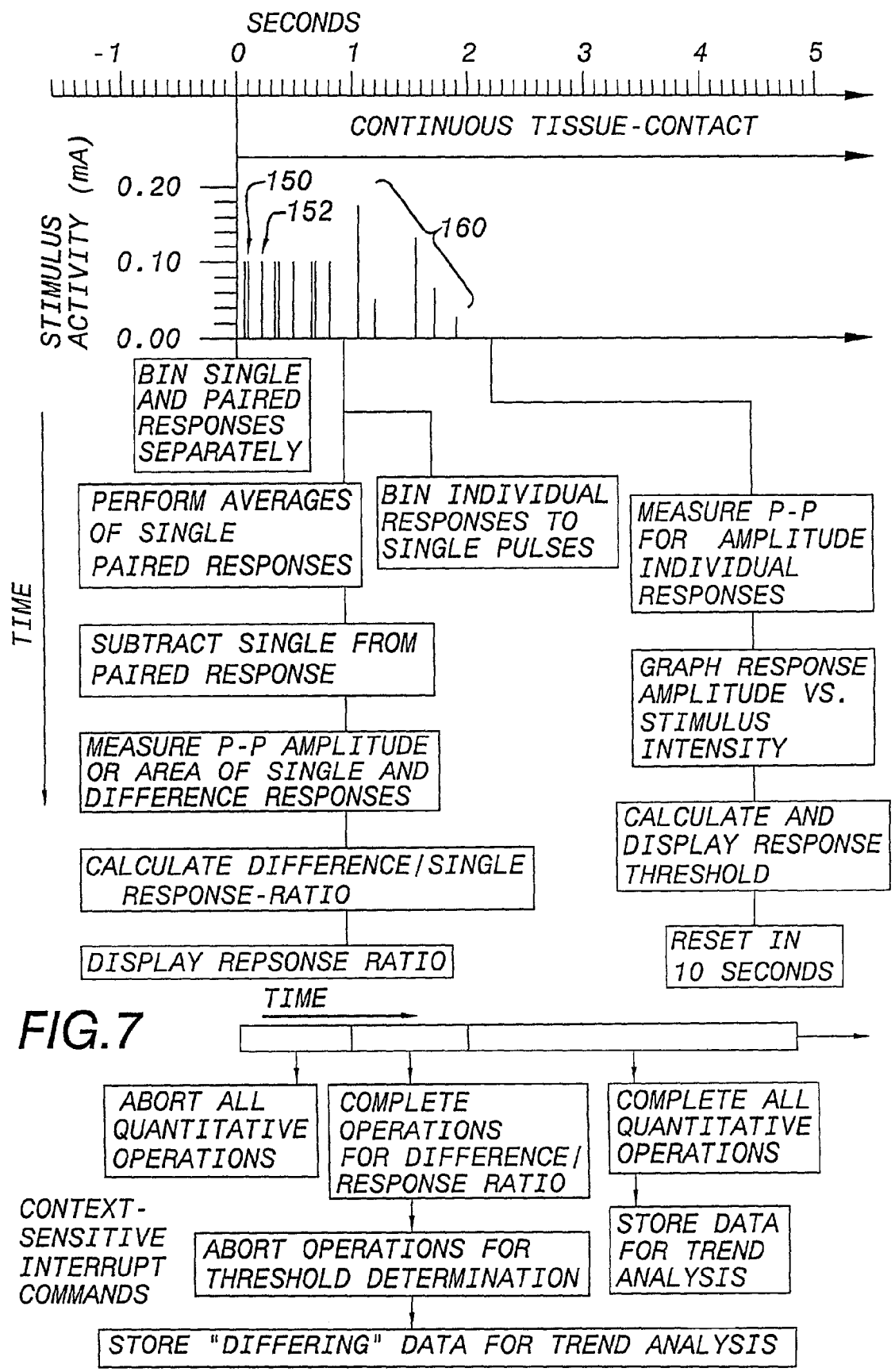
FIG. 7 is graphical representation of a pre-programmed set of electrical stimulus pulses of varying intensities used in the intraoperative monitoring of responses to stimulus pulses, in combination with a flow diagram illustrating the steps in the TCI-time line algorithm and the context sensitive interrupt commands for controlling whether the TCI time line algorithm is aborted or completed.
Figure 8:
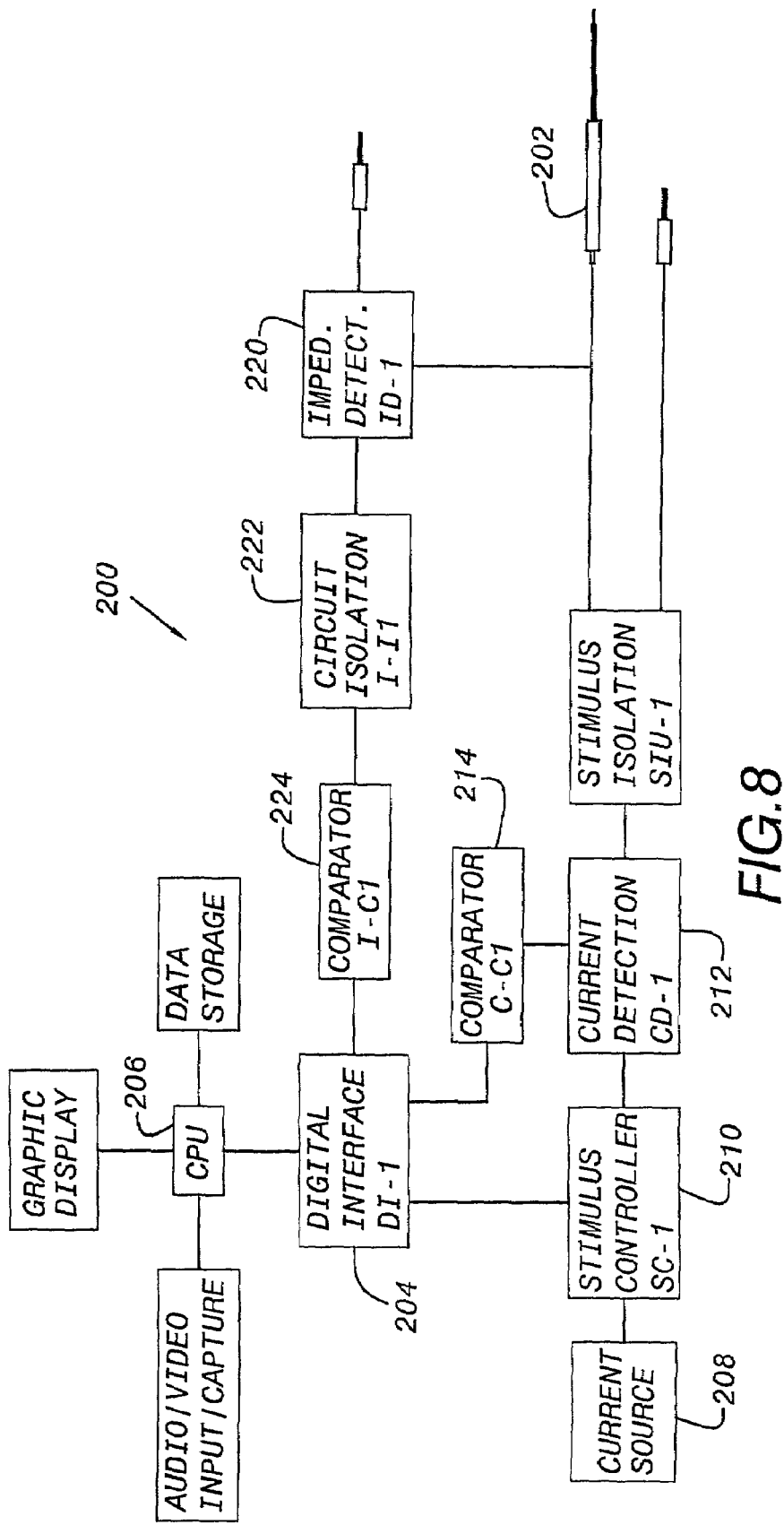
FIG. 8 is a block diagram of the intraoperative neurophysiological monitoring system TCI-Time line algorithm controlled impedance and current flow detection circuit, in accordance with the present invention.
Figure 9:
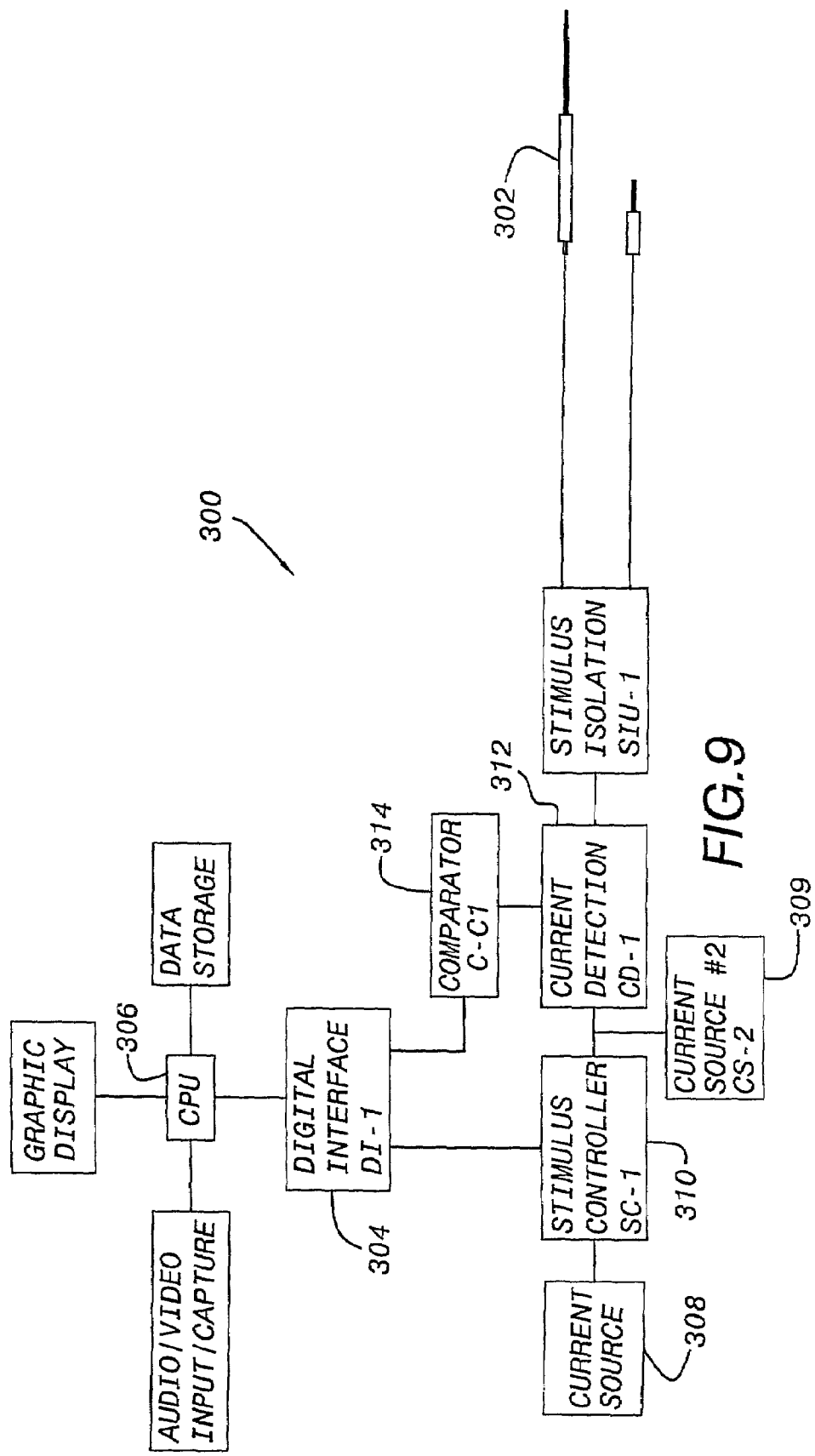
FIG. 9 is a block diagram of the intraoperative neurophysiological monitoring system TCI-Time line algorithm controlled current flow detection trigger circuit, in accordance with the present invention.

Turning now to FIGS. 7, 8 and 9, another aspect of the present invention relates to a versatile, precise and ergonomic method of control for multiple data-management procedures associated with intraoperative neurophysiological monitoring. The method (discussed above in conjunction with the TCI time line algorithm) involves digital control of a preprogrammed array of electrical stimuli and a coordinated series of data acquisition, analysis, display and storage algorithms initiated through the detection of the temporal pattern of electrical stimulus probe use and is particularly advantageous in the field of intraoperative electromyographic (EMG) monitoring in association with periods of electrical stimulus probe use. Certain aspects of the control system may be linked to supra-threshold detection of EMG or artifact activity. Moreover, the method and algorithm may be adapted to other fields in which a probe is used for data acquisition and where data-management operations can be linked to monitored aspects of its use.

FIG. 7 is a graphical representation of a pre-programmed set of electrical stimulus pulses of varying intensities used in the intraoperative monitoring of responses to stimulus pulses, in combination with a flow diagram illustrating the steps in the TCI-time line algorithm and the context sensitive interrupt commands for controlling whether the TCI time line algorithm is aborted or completed. FIG. 8 is a block diagram of an intraoperative neurophysiological monitoring system 200 with a TCI-Time line algorithm controlled impedance and current flow detection circuit, and FIG. 9 is a block diagram of an alternative, simpler embodiment including an intraoperative neurophysiological monitoring system 300 with a TCI-Time line algorithm controlled current flow detection trigger circuit, in accordance with the present invention.

Referring now to the upper portion of FIG. 7, showing a graphical representation of a pre-programmed set of electrical stimulus pulses of varying intensities used in the intraoperative monitoring of responses to stimulus pulses, the vertical axis is graduated. in milliamps (mA) of stimulus current applied through a stimulus probe and the horizontal axis overhead is a time scale in seconds. A preprogrammed pattern or paradigm of stimulus pulses, as illustrated, preferably includes a first pair 150 of stimulus pulses spaced at less than 100 mS apart and having equal amplitudes of approximately 0.10 mA. These are called paired pulses 150 and are followed at a spacing of approximately 100 mS by a single pulse 152 having an equal amplitude, 0.10 mA. Preferably, the pattern next includes another set of paired pulses 150, followed in alternate succession by another single pulse 152.

The steps of the algorithm are illustrated in the center portion of FIG. 7, in which later steps are below the step before. The TCI-algorithm has two parallel or simultaneous processes, as will be described in greater detail below.

Returning to FIG. 8, intraoperative neurophysiological monitoring system 200 includes current source 208 which generates stimulus current and is connected to the stimulus controller 210 which controls the intensity, duration and temporal patterns of delivered stimulus pulses. Controller 210 is, in turn, responsive to and controlled by a digital-interface (DI-1) 204. Current-flow is measured for each stimulus output by a current-flow detection circuit 212, the output of this circuit will be used to drive the digital-readout of current-flow for the corresponding stimulus output. The output of the current flow detection circuit 212, relating to measured current-flow, is compared against the user selected level by a comparator circuit 214, and if the value falls within predetermined limits (90–95%), the comparator circuit 214 optionally puts out an "enable" signal, to be used to trigger an "adequate-current" speech sample or tone; it may also be incorporated as an "enable" signal for the TCI-Time line. Digital-interface 204 stores various stimulus-paradigms, which are initiated in a pre-programmed fashion (TCI-Time line) by detection of tissue contact. The digital interface also directs data capture, analysis, display and storage in a preprogrammed fashion per the TCI-Time line. The interface consists of two components, one of which is located in the main unit, the other of which is located in a PCI-bus slot in the computer.

For output #2, #3 or both, the digital-interface may be configured to input measured-values of stimulus-circuit impedance and make pre-programmed adjustments of stimulus intensity, based upon impedance values. It is anticipated that stimulus output #1 will be used with a flush-tip stimulus probe for which such an application is not necessary. Impedance detection circuit ID-1 220 provides an indication of tissue contact and a measurement of stimulus-circuit impedance. Detection of tissue contact can be used to initiate the TCI-Time line and measurement of impedance can be used to provide a "qualitycheck" of the stimuluscircuit integrity and provide a means of adjusting stimulus intensity to the level of current-shunting. For impedance measurement, the impedance-detection circuit provides a small, sub-threshold signal that is detected to establish continuity. Patient connections for impedance detection circuit 220 are electrically or optically isolated by isolation circuit 222. A comparator 224 receives output from impedance detection circuit 220 and computes scalar representations or values of stimulus circuit impedance and provides an output digital interface 204 to drive the various data-handling operations and preprogrammed stimulus intensity adjustments. Digital interface 204 connects the stimulator with a CPU 206, so that data acquisition, analysis, display and storage can be coordinated. Digital interface 204 and CPU 206 execute spreadsheeting of data and drive a graphic display 208 (e.g., a CRT or LCD). Digital interface 204 is preferably configured to direct the capture of digitally-sampled audio and video data corresponding to signal data. CPU 206 is preferably programmed to store files for later retrieval and "off-line" analysis.

As shown in FIG. 9, intraoperative neurophysiological monitoring system 300 includes current source 308 which generates stimulus current and is connected to the stimulus controller 310 which controls the intensity, duration and temporal patterns of delivered stimulus pulses. Controller 310 is, in turn, responsive to and controlled by a digital-interface (DI-1) 304. Current-Source #2, CS-2, 309 injects a small, continuous, sub-threshold current as a probe signal to provide means of tissue-contact detection. Current flow is measured for each stimulus output by a current-flow detection circuit 312. The output of this circuit will be used to drive the digital-readout of current flow for the corresponding stimulus output. The output of the current flow detection circuit 312, relating to measured current flow, is compared against the user selected level by a comparator circuit 314, and if the value falls within predetermined limits (90–95%), the comparator circuit 314 optionally puts out an "enable" signal, to be used to trigger an "adequate-current" speech sample or tone; it may also be incorporated as an "enable" signal for the TCI-Time line.

As noted above, quantitative measurements of nerve function in intraoperative monitoring are relatively cumbersome and require involvement of technical personnel to change stimulator settings and various recording parameters in order to acquire, analyze, display and store data. The applicant has noted that there are not many types of quantitative measurements regarding nerve function assessment, however, and that threshold and peak amplitude measurements are the most widely used. The applicant has also discovered that paired stimuli pulses 150 are particularly effective when assessing nerve fatigue. Operating surgeons usually have specific preferences regarding the type of quantitative data to be collected and analyzed during the course of a given surgical procedure, so there is little need for "on-the-fly" flexibility in the operating room (OR) when performing quantitative data collection.

Quantitative data on nerve function is mainly acquired through the use of an electrical stimulus probe (e.g., 202 or 302, as shown in FIGS. 8 and 9), provoking electromyographic responses for quantitative analysis.

The inventor has observed that surgeons use the stimulus probe (e.g., 202) differently for locating and "mapping" than for quantitative analysis of the functional status of nerves of interest. Temporal aspects of stimulus probe use can be monitored by the tissue contact detection capability within the digital stimulator as described previously. A signal is generated in the stimulator that relates to the period of continuous contact of the stimulator probe with patient tissue. The signal continues as long as continuous tissue contact is maintained and is delivered to a system controller, which is able to initiate multiple predetermined sequential and parallel operations within the nerve integrity monitor, as shown in the central flow chart portion of FIG. 7. These operations relate to delivery of preprogrammed stimulus sequences and to the acquisition, analysis, display and archival storage of EMG data. Whether the predetermined operations are initiated or completed depends upon the duration of continuous tissue contact. For example, as shown in the flowchart portion at the bottom of FIG. 7, if the duration of continuous tissue contact is less than a preselected period of approximately one or two seconds, the controller will maintain the operational status of the nerve integrity monitor in the "search" mode. However, if the duration of continuous tissue contact exceeds the preselected time period, the stimulator or controller may alert the surgeon with an indicator tone and the controller will automatically change the operational status of the nerve integrity monitor to a quantitative assessment mode and provide a preprogrammed sequence of quantitative assessment stimulus pulses 160, as shown in the upper portion of FIG. 7. A monitoring indicator tone may also be designed or configured to signify whether adequate current and/or stimulator circuit impedance has been achieved, as an indication of quality assurance, as discussed above. From the time of tissue contact detection, a digital clock is initiated, controlling a preprogrammed sequence of events through a controller interface DI-1 (as shown in FIGS. 8 and 9). For the purposes of this description, the period of continuous tissue contact of the stimulus probe is termed the "dwell" or "dwell time", and the series of preselected operational changes provoked by the "dwell" is termed, the "Tissue Contact Initiated Event Sequencing Time line" or"TCI-Time line" and is illustrated, in part, in the middle and lower flow charts included in FIG. 7. The control method to be described is designed for use with the main stimulus probe (e.g., probes 202, 302 connected to stimulus output #1 in a multi-stimulus output system, as described above) and may be used to control all functions of the nerve integrity monitor in a preselected fashion, by execution of an algorithm stored in memory. The described methodology need not be limited to medical applications, in that the use of any probe, where its period of dwell can be measured, may be similarly configured to control multiple functions. The following description involves the preferred embodiment, although many possible sequence strategies are available through the TCI-Time line:

Through the associated controller and controller interface (e.g. the Digital interface DI-1 204, of FIG. 8 and 304, of FIG. 9), the onset of dwell causes the artifact-detection circuit to be suspended ("defeated") throughout its duration and a preset pattern of stimulus pulses, the intensity of which is determined by front panel controls, will be delivered through the stimulator probe for locating and "mapping" the physical contour of the nerve of interest. After a preselected dwell time of approximately one second (as shown in the upper part of FIG. 7), front panel control of stimulus parameters is defeated, the pattern of stimuli is changed from single pulses 152 to alternating paired pulses 150 with single pulses 152, the intensity of which is somewhat greater (supra maximal), and the provoked EMG responses are digitized and individually captured into stable buffers. If the dwell is interrupted before a dwell of 2 seconds, the TCI-Time line is inactivated or aborted, the artifact-detection circuit is enabled, the stable buffers are cleared of captured signal and pulsed stimuli are no longer delivered through the stimulus probe. After a 2 second preselected period of dwell, the controller and associated interface initiate a signal processing sequence, where the captured responses in stable buffers are analyzed by averaging the single and paired responses separately and computing the difference between the paired and single response by digital subtraction. The magnitude of the single and digitally subtracted responses are computed and compared. A scalar value relating to a ratio of the magnitudes of the digitally subtracted response and the single response is stored in a spreadsheet against the absolute or lapsed time (of the operation) and is displayed by CRT output automatically or upon an input "request" by the operating surgeon. The stable buffers used in these computations are automatically cleared at completion. The above computational operations occur in parallel to the following:

After a 2 second preselected period of dwell, the controller and interface defeat front panel control of stimulus parameters and alter the stimulus delivery pattern to a series of single pulses of varying intensity 160. The controller and interface direct the provoked EMG responses to be captured individually into stable buffers. If the dwell is interrupted prior to completion of the stimulus sequence, the TCI-Time line is discontinued, the sequence of stimulator pulses is discontinued, the stable buffers are cleared of captured signal, the artifact-detection functions are enabled and stimulus parameters are reverted to front panel controls. However, interruption of the dwell after 2 seconds does not interfere with the completion of the parallel operations described above regarding the mathematical treatment of EMG activity-provoked by single and paired stimulus pulses.

If the dwell is continued (after 2 seconds), then until the stimulus sequence is completed, the stimulator or TCI-Time line controller delivers a second indicator tone and the controller and interface initiate a series of operations to generate a scalar value of response threshold. Each individually captured EMG response is analyzed for power content (peak or average), the scalar value of which is stored in a spreadsheet in conjunction with the stimulus intensity used to provoke it. The spreadsheet data relating to all stimulus intensities and corresponding responses is used to compute (or estimate) the stimulus intensity in milliamps (mA) at which half-maximal response magnitude (power) occurred. This scalar value (in mA) is then defined as the "response threshold" and is applied to a spreadsheet against absolute or lapsed time of the surgical procedure. The scalar value or a graphical plot of threshold versus operative time may be displayed automatically by CRT screen or displayed upon request by input supplied by the operating surgeon. These computational operations are carried out in parallel with progress of the dwell and may reach completion considerably after the dwell has been interrupted.

As described, the "TCI-Time line" is a multidimensional control algorithm or device utilizing information spanning both time and space. The continuous tissue contact dwell serves to initiate various series of operations through the TCI-Time line controller and interface. These operations may include simple or complex stimulus delivery paradigms, and corresponding data acquisition, analysis, display and archival storage procedures. The stimulation sequences and data handling algorithms proceed along different time lines, as per pre-programmed, parallel (processing) software algorithms. As long as the dwell continues, these operations proceed to completion in sequence. Alternatively, interruption of the dwell aborts all subsequent initiation of events along the dwell, but may allow some of the previously initiated events to reach completion as described above. The TCI-Time line controller directs operational events in different locations within the nerve integrity monitoring device. Production of stimulus pulses occurs in the stimulator portion of the monitor, while data acquisition, analysis, display and storage may occur in different locations, such as on the memory of a PCI card, CPU RAM memory or a hard drive. Thus the present TCI-Time line control system must account for multiple time dimensions and multiple locations within the monitoring device.

Detection of tissue contact is preferably achieved by continuous stimulator circuit impedance measurement or continuous measurement of current flow with use of a separate sub-threshold current delivered downstream from actual pulsed stimuli to the patient. Either of these methods will allow the detection of the temporal pattern caused by tapping the stimulator probe two or three times onto patient tissue (away from important structures) as a means of providing additional input to the controller through the tissue contact detection circuit. A "double" or "triple" tap of the stimulus probe may be preselected for altering the normal operation of the controller, such as initiating a display of previously stored data as a "time trend." That is, a "double tap" command may provoke the controller to display a time trend of a measured parameter, such as response threshold. The scalar value of stimulus intensity (mA), where the response threshold is achieved, is plotted against time (duration of the operation) to give the surgeon a clearer impression of how the nerve of interest has responded throughout the surgical procedure.

Optionally, the control capabilities of the TCI-Time line are used for analyzing and storing data derived from detection of supra threshold events. Supra threshold events may be transferred from stable buffers, described previously with regard to "additional DSP" analysis of supra threshold events, and converted to file format for archival storage. The file of the digitized signal, its scalar DSP values (e.g., peak and average rRMS), and its channel number (or identity) may be archived (as in a spreadsheet) against the absolute or lapsed (operative) time of its appearance for later (off-line) retrieval. Such capabilities improve the ability to "tune" DSP parameters for greater accuracy in detecting appropriate events for analysis, for alerting the operating surgeon and for distinguishing artifacts from true EMG.

Preferably, audio and video capture devices are integrated into the system to perform audio and video data capture functions. An independent method of distinguishing artifact and EMG supra threshold events is to interpret events in the context of the surgical procedure. If the supra threshold event occurred exactly at the time of a surgical manipulation, it may be interpreted as a mechanically stimulated (hence non-repetitive) EMG event. Alternatively, if the event appears to occur independently of surgical manipulations, it is interpreted as either artifact or non-localizing (repetitive) EMG. Relatively brief (3–5 seconds) periods of digitized audio signal of the sound delivered to the surgeon through the loudspeaker in the nerve integrity monitor and digitized video of the surgical procedure, from a (microscope or hand held) camera monitoring the surgical field, is adequate to interpret the "context" of a supra threshold event. Audio and video signal may be digitized and held in FIFO "scroll" buffers within the nerve integrity monitor. For investigational purposes, the logical circuits used for detection of supra threshold events may send a signal to the TCI-Time line controller when certain preselected supra threshold events are detected; the signal provokes the TCI-Time line controller to cause the capture of digitized audio and video for an interval starting 2–4 seconds before and ending one second after the onset of the supra threshold event. The captured audio and video can then be converted to file form (*.avi, *.mpg or equivalent) and archived along with the signal data mentioned above. Such capability tremendously facilitates evaluation (validation) of various methods of event (artifact and EMG response type) detection for accuracy and effectiveness.

With the present control system, temporal aspects of stimulus probe use can be made to control an entire quantitative analysis paradigm in a pre-programmed, preset manner, based upon the needs of the user. This will involve a mix of sequential and parallel operations and smooth operation is dependent upon a seamless digital CPU interface (e.g., 204 or 304) for control of data acquisition, analysis and display, preferably in a Windows® based software system. The algorithm steps or command sequences and interrupt interpretations are stored on non-volatile memory, such as EEPROM or "flash memory," providing fast online operation in a controller which is readily reprogrammed or modified off-line by CPU-interface. At present, the prevailing standard digital interface is the Peripheral Components Interface (PCI); it is to be understood that future developments may provide equivalents to the PCI standard. Accordingly, the following discussion is a description of but one exemplary embodiment which happens to include a PCI circuit card.

The enhanced or "complete" neurophysiological monitoring system 200 (as shown in FIG. 8) consists of the basic monitoring unit, a processor 204 including a CPU 206 (e.g., an Intel Pentium® brand microprocessor) and a Peripheral Components Interface (PCI) circuit card. CPU 206 interfaces with the basic monitoring unit through the PCI for both off-line and on-line operations. Digitized signals from the basic monitoring unit are continually delivered (e.g., via an optical transmission link) to the PCI card, which continually routes them to temporary scroll buffers. When triggered by the tissue contact initiated (TCI) Time line or by detection of evoked EMG responses, recorded signal events are "captured," along with time, data channel identification and other relevant information. The captured signals are held in a stable buffer for DSP manipulations (e.g., Fast Fourier Transform (FFT) frequency conversion) and for conversion to a selected file format. A scroll buffer is a first-in-first-out (FIFO) image buffer storing the most recent waveform segment; the stored segment has a selected duration (e.g., approx. 2–10 seconds). A stable buffer (or bin) is also an image buffer but only holds discrete supra-threshold waveforms or events, and so effectively ignores the waveform trace between events; the stable buffer holds waveforms of selected durations or epoch lengths (e.g., approximately 1 second).

The PCI interface includes the scroll buffers and the stable buffers containing captured signal data for quantitative facial nerve signal assessment. Associated DSP circuitry is located on a PCI circuit board. There must be a relatively generous number of stable buffers (or bins) available to separately capture one or more given EMG events on multiple channels and to capture individual responses relating to stimuli of differing parameters (intensities). Additional buffer spaces or bins must also be available for digital subtraction functions, where a "third" bin stores the computed difference between two others for further quantitative analysis. The total number of bins must be adequate to handle a variety of analysis algorithms.

There must also be consideration for how signals occurring simultaneously or nearly simultaneously will be processed. The individual bin size must be adequate to store a large number of samples, thereby providing adequate waveform fidelity and the sample rate or time-base must be high enough to capture signals with the required accuracy.

The processor includes a motherboard having a CPU for acquisition of scalar data from the DSP circuits on the PCI-card and for data presentation functions such as spreadsheeting and graphing (e.g., using Lotus® or Excel® spreadsheet programs) and for controlling the display. The processor is preferably also configured to create, tag and bundle data files from the temporary stable buffers on the PCI card. Image data files are preferably bundled with corresponding "captured" audio and video files (from separate video and sound cards) and then transferred into permanent storage in appropriate locations on the processor hard drive for later review. Off-line, saved data is readily re-loaded into temporary stable buffers to permit the surgeon to review or re-analyze data to observe the effectiveness of artifact recognition and nerve function assessment.

Thus, the system delegates DSP functions to various components for rapid performance of mathematical operations and display of data. Complex stimulation paradigms in the form of software algorithms are initiated by a digitally controlled stimulator, based upon temporal aspects of tissue contact by the main stimulus probe. The digital stimulator (or the controller executing the TCI-Time line algorithm) sends simultaneous signals through the PCI-interface to direct data to the appropriate buffers (or bins) for on-line analysis. Additional signals, either from the basic monitoring unit or internally generated on the PCI by pre-programmed algorithms, initiate pre-set data-display and data storage algorithms. Six to twelve different stimuli and a corresponding number of storage buffers may be employed for threshold detection. Alternating paired and single pulses will require at least three bins: one each for binning responses evoked by paired and single pulses, and a third for holding computed digital subtraction data. Optionally, within the two bins for single and paired responses or by combining the results of separate bins, repetitious responses may be used to compute a signal "average" for single and paired responses. The respective averages may be used to compute the digital subtraction data for the "third" bin.

Complete control over on-line operations of the intraoperative neurophysiological monitor of the present invention can be achieved through the use of the TCI-Time line and is preferably set up off-line using keyboard and mouse input devices through a standard personal computer operating system such as Microsoft Windows® software.

In the preferred embodiment, all changes made by off-line input procedures are transferred to the main unit of the nerve integrity monitor and "burned in" to non-volatile (EEPROM or flash) memory. As a result, the information transferred will be protected from spurious voltage spikes and accidental unplugging. This is distinct from prior art methodology, where off-line changes are stored in volatile memory, which may be susceptible to spurious voltage spikes and accidental unplugging of equipment.

Additional on-line flexibility is afforded through use of simple input devices which are convenient and easy to use, but not as comprehensive as the keyboard and mouse combination; in one embodiment, the stimulus probe is used as a pointing device for inputs to the controller, as will be described in greater detail, below.

Yet another aspect of the present invention is an adaptable threshold level setting method for use during intraoperative neurophysiological monitoring and is also intended to enhance detection of brief episodes of EMG activity, provoked by mechanical or electrical stimuli. The method improves the performance and accuracy of the above described artifact-detection strategy, based upon response distribution among "intelligent" and "non-intelligent" electrodes.

Threshold-detection is based on measured signal power (such as root-mean-square) for each channel. As signal power increases, the threshold is automatically elevated in order to avoid threshold detection of background EMG activity. One embodiment of this method is to sample signal-power at intervals, and to hold the determinations in temporary memory, such as in a digital scroll method. In order for a supra-threshold, signal event to be detected, one or more consecutive signal power determinations would have to be greater, by a preset difference level, than the signal power sampled one second before them. An alternative is to require that one or more consecutive signal-power determinations be greater than the power levels one second before and one-second after, thereby limiting threshold-detection to just brief responses.

Figure 15:
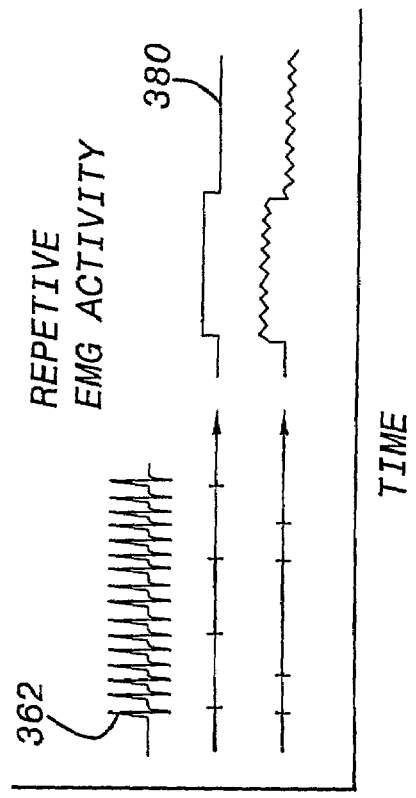
FIG. 15 is a set of related waveform traces, plotted with voltage as a function of time, illustrating a sensed repetitive EMG signal of a duration including first and second probe sampling windows of selected durations, and the Rectified RMS power derived from the difference detection algorithm, for first and second probe sampling window durations.
Figure 14:
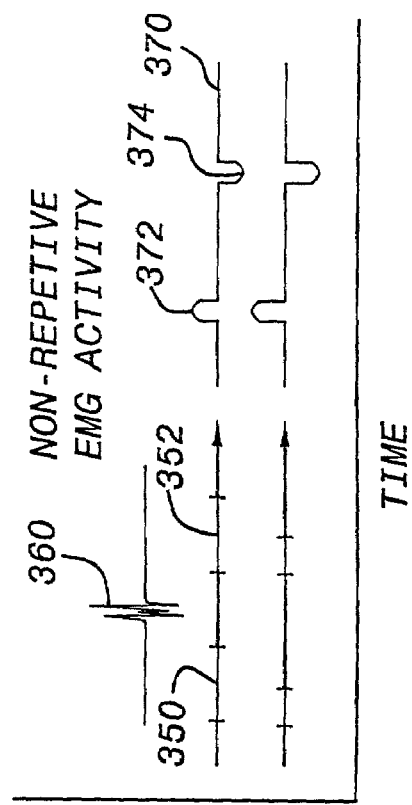
FIG. 14 is a set of related waveform traces, plotted with voltage as a function of time, illustrating a sensed non-repetitive EMG signal temporally situated between first and second probe sampling windows of selected durations, and the Rectified RMS power derived from the difference detection algorithm for first and second probe sampling window durations.
Figure 16:
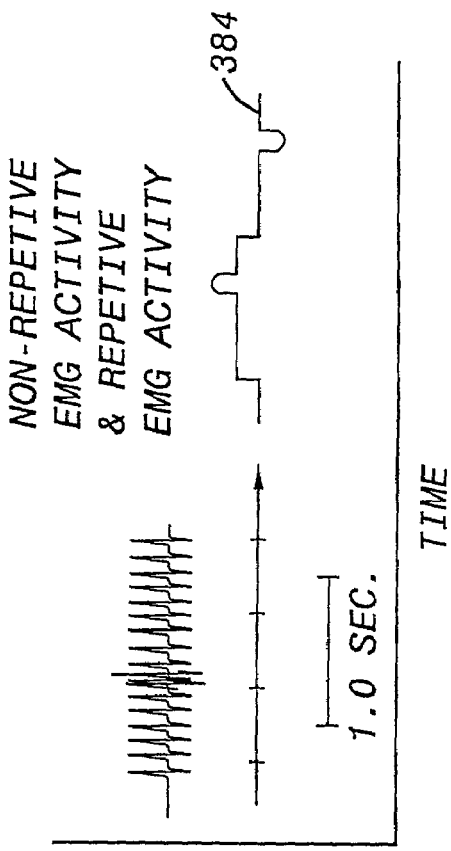
FIG. 16 is a set of related waveform traces, plotted with voltage as a function of time, illustrating a sensed non-repetitive EMG signal temporally situated between first and second probe sampling windows and superposed on a sensed repetitive EMG signal of a duration including the first and second probe sampling windows, and the Rectified RMS power derived from the difference detection algorithm, for a selected probe sampling window duration.

In an alternative and preferred embodiment the thresholding could be performed in conjunction with determination of the likelihood that an observed event is non-repetitive EMG activity instead of the more noise-like repetitive EMG activity. The method includes defining "probes" or sampling windows of time which stored waveform traces are passed through. FIG. 10 is a set of related waveform traces, plotted as a function of time, illustrating first and second probe sampling windows 350, 352 each of a selected duration and temporally spaced at a selected inter-probe interval 354. FIG. 11 is a waveform trace, plotted with voltage as a function of time, illustrating a non-repetitive EMG activity 360, and FIG. 12 is a waveform trace, plotted with voltage as a function of time, illustrating a repetitive EMG activity 362. FIG. 13 is a set of related waveform traces, plotted with voltage as a function of time, illustrating a non-repetitive EMG activity 360 superposed on (or occurring and sensed simultaneously with) a repetitive EMG activity 362. FIG. 14 is a set of related waveform traces, plotted with voltage as a function of time, illustrating a sensed non-repetitive EMG signal temporally situated between first and second probe sampling windows of selected durations, and the Rectified RMS power derived from the difference detection algorithm for first and second probe sampling window durations; and FIG. 15 is a set of related waveform traces, plotted with voltage as a function of time, illustrating a sensed repetitive EMG signal of a duration including first and second probe sampling windows of selected durations, and the Rectified RMS power derived from the difference detection algorithm, for first and second probe sampling window durations. FIG. 16 is a set of related waveform traces, plotted with voltage as a function of time, illustrating a sensed non-repetitive EMG signal temporally situated between first and second probe sampling windows and superposed on a sensed repetitive EMG signal of a duration including the first and second probe sampling windows, and the Rectified RMS power derived from the difference detection algorithm, for a selected probe sampling window duration. As discussed above, the intraoperative neurophysiological monitoring system also includes an enhanced method and algorithm for detecting or thresholding non-repetitive EMG events or activity (such as the short duration pulses 360 indicative of EMG activity) as distinguished from a repetitive EMG activity waveform 362, even when the non-repetitive EMG events are sensed simultaneously with the repetitive EMG events, in which case the waveforms are superposed upon one another as shown in FIG. 13. The enhanced threshold detection algorithm includes the steps of buffering or storing a continuous series of samples of the sensed EMG waveforms from one or more sensing electrodes (e.g., 130); the buffered waveform is processed by running the stored waveform samples serially through spaced probe first-in-first-out (fifo) sampling windows of selected duration and having a selected temporal spacing therebetween; in the preferred embodiment, the probe sampling windows (e.g., 350, 352) have a duration in the range of 0.25 seconds to 0.5 seconds and the beginning of the first probe sampling window is temporally spaced (with an inter-probe interval 354) at one second from the beginning of the second probe sampling window. The algorithm passes the stored waveform samples serially through first probe sampling window and then through the second probe sampling window. As the stored waveform samples (e.g., 360) pass through each probe sampling window (350, 352), a scalar value corresponding to the rectified RMS (rRMS) power of the waveform is generated. As best seen in FIGS. 14, 15 and 16, the algorithm continuously computes a threshold value by subtracting the instantaneous value of the second probe sampling window rRMS power from the first probe sampling window rRMS power; the continuously generated results of this computation are readily plotted as a threshold value waveform 370. Since the algorithm passes the stored waveform samples serially through the first probe sampling window and then through the second probe sampling window, a non-repetitive EMG activity will produce the threshold value waveform 370 (of FIG. 14) having a first, positive going pulse 372 having a width approximating the duration of the non-repetitive EMG activity 360 (corresponding to the first probe sampling window rRMS power) and then a second negative going pulse 374 having the same width (corresponding to the subtracted second probe sampling window rRMS power).

Alternatively, as best seen in FIG. 15, a repetitive EMG activity 362 having a duration longer than the selected (1.0 second) spacing between the probe sampling windows produces a threshold value waveform 380 having only one positive going pulse having a width approximating the duration of the interval beginning at the start of the first probe sampling window 350 and ending at the start of the second probe sampling window 352 (in the present example, a duration of one second). For a stored waveform having a non-repetitive EMG activity superposed on a repetitive EMG activity, as shown in FIG. 16, the algorithm will produce a threshold value waveform 384 having a first one second long pulse including a second positive going pulse having a width approximating the duration of the non-repetitive EMG activity (corresponding to the first probe sampling window rRMS power) and then a second negative going pulse having the same width as the non-repetitive EMG activity (corresponding to the subtracted second probe sampling window rRMS power).

Whenever the enhanced threshold detection algorithm produces a threshold value waveform including a first positive going pulse followed by a second negative going pulse, there is an indication that a brief (e.g., <1.0 sec) response has occurred which may be either localizing non-repetitive EMG or artifact. Detection of such an event provokes the artifact-detection circuitry to evaluate its spatial distribution among "intelligent" and "non-intelligent" electrodes and (optionally) additional DSP algorithms in order to determine its status as an artifact or (localizing) EMG event. The surgeon is then prompted with an appropriate audible and (optionally) visual annunciation.

Insofar as monitoring instrument use is concerned, additional on-line flexibility is afforded through use of simple input devices which are convenient and easy to use, but not as comprehensive as the keyboard and mouse combination; in one embodiment, the stimulus probe (e.g., 202) is used as a pointing device for inputs to the controller. During surgery, or when "on-line", an electrical stimulus probe is preferably employed as a convenient controller input device and the TCI-Time line algorithm controls most on-line system operations, including which data are displayed to the operating surgeon on the CRT screen display, however, the surgeon may periodically want to see additional information, such as a display of a measured parameter graphed as a function of time, over course of the procedure. The stimulus probe provides a convenient and simple input device for initiating such requests, since the surgeon is likely already holding the probe, and so need not put the probe down to use a keyboard, or the like. The TCI-Time line algorithm is triggered upon detection of tissue contact by the electrical stimulus probe. Tissue contact detection includes probe signal current flow or impedance-change detection.

In addition to providing an indication of presence or absence of tissue contact, the tissue contact detection apparatus is configured to recognize specific signatures, such as a "double tap" or "triple tap" of the-stimulus probe against non-sensitive patient tissue within the surgical field. The detection of these predetermined signatures can be used to provide additional online input to the TCI-Time line controller. When such a pattern is detected, a separate signal is sent to the TCI-Time line controller for initiation of context sensitive, predetermined commands, a sequence analogous to a "double click" of a standard mouse when pointing to an icon in a Windows® compatible program. The identity of these commands are changeable, depending upon the monitoring context of the request; context is provided by the TCI-Time line algorithm. If the "double-click" occurs before the completion of a TCI-Time line controlled operation, the request is interpreted differently than for a double-click occurring after completion.

The tapping pattern can differ among different users, in order for the tapping pattern of a given user to be recognized, a setup algorithm includes an adjustment method allowing the user to input his or her individual tapping pattern. Recognition of tapping patterns may be performed by "default" recognition settings within the tissue contact detection circuitry. However, because the temporal aspects of tapping may vary significantly among individual surgeons, the preferred system allows an individual surgeon's tapping signature to be captured for later recognition. It is preferred that this is performed early in the surgical procedure, before critical stages. For this procedure, a front panel or foot pedal switch is depressed, immediately after which the surgeon performs a "double tap" or "triple tap" signature. The pattern of impedance change or current flow change detected by the tissue contact detection circuitry is stored and used as a template for recognition of similar "signature" patterns at a later time.

Also, when the double- or triple-tap input command is used, a sound sample or audible annunciation is preferably activated to indicate that the intended command has been successfully communicated. The sound sample can be any form of effective audible feedback to the user (e.g., a sound of a standard mouse double-click or triple-click).

A double tap is defined as a first probe contact having a first, short duration (e.g., less than one second) followed by an interval in which the probe is lifted and not in contact with anything and having second, short duration (e.g., also less than a second) and followed by a third probe contact having a third, short duration (e.g., less than one second). A computer executable algorithm (preferably part of the TCI-Time line algorithm) for detecting and responding to the double tap sequence is readily prepared and responds to sensed current or impedance changes indicating the one, two or three taps has occurred, and then, in response, triggers execution of a desired monitoring or data handling or display oriented command.

After completion of a TCI-Time line controlled, pre-programmed stimulus sequence with corresponding quantitative data display, the algorithm preferably includes program steps for detecting a stimulus probe double-tap and, in response, displaying all similar measurements obtained from the beginning of the procedure (e.g., traced as a waveform showing voltage as a function of time), wherein a time-trend of stimulation threshold can be observed to detect a significant injury in progress. Similarly, after supra-threshold detection of an EMG response, the algorithm may include "if then" condition detection program steps wherein detection of a "double tap" is the input causing a display of the IDSP data for that response or for a display of a DSP-derived parameter, such as root mean square (RMS) power, as a function of time. Such a trend may show a loss of signal power over the course of the procedure and may indicate a fatigue trend in the nerve under observation in response to ongoing mechanical manipulations.

A simple input device used in conjunction with the TCI-Time line algorithm alternatively includes two or three button operated switches accessed from a cylindrical handle. The two button configuration may be used in a manner similar to setting of a watch; one button selects options from a menu displayed on the nerve integrity monitor and the other button is used to choose a user preference or selection from the menu of options. Alternatively, a three-button input device provides more flexibility with forward and backward movement through a menu or series of menus, since the buttons could be used to scroll up, scroll down or select an option, respectively. The simple input device is readily kept sterile in the operative field and its simplicity allows rapid data or control input and ease of use. Such a device does not require the use of the stimulating probe.

The above described simple devices for on-line use provide input through the monitoring system controller digital interface, rather than through a serial port of the host computer. Off-line operations, controlled by keyboard and mouse, preferably operate through mouse and keyboard ports on the controller CPU.

Turning now to another aspect of the present invention, a squelch control method is provided for use during multi-channel intraoperative neurophysiological monitoring for the purposes of enhancing the surgeon's ability to hear brief localizing (non-repetitive) electromyographic responses during periods of significant background activity. The squelch control method is based upon the method for detecting repetitive EMG activity made possible by the enhanced threshold detection strategy described above. Data from all (and exclusively) "intelligent" EMG channels is digitized and monitored by the enhanced threshold detection circuit, employing two probe windows as described, with an inter-probe interval of approximately one second. By DSP, the average rRMS is continuously computed for both windows and the scalar value is referenced against electrical silence. With the two probe window strategy, if only one window is active at a time, the duration of a supra threshold event must be less than the inter-probe interval. If both windows are active simultaneously, the duration is equal to or greater than the inter-probe interval. Since the vast majority of non-repetitive activity is less than one second in duration, an interprobe interval of one second is able to effectively distinguish repetitive and non-repetitive responses. Repetitive responses are detected when both probe windows are simultaneously active.

In the "automatic" embodiment of the present invention, the scalar values of average rRMS derived from the two probe windows are continuously scanned by a software comparator constructed in non-volatile memory. The comparator is configured to compare ongoing average rRMS values against a user preselected threshold value. If the threshold value is exceeded in both probe windows, a signal is generated which activates a muting switch to eliminate that particular channel from the audio (loudspeaker) signal to the operating surgeon. If other channels reach supra threshold levels of continuous repetitive EMG activity, more channels may be muted, except the last (quietest) channel. That is, no matter how much repetitive activity, at least one "intelligent" channel is preserved for continuous audio display of EMG signals to the operating surgeon. When the average rRMS values of both windows decrease below threshold levels, the muting switch is automatically disabled.

In an alternative embodiment, the muting function can be enabled manually. Some surgeons may prefer to decide on a "case by case" basis, when to begin muting offending EMG channels. When bothered by persistent repetitive EMG activity, the surgeon may request that a nurse or technician depress a momentary push-button switch, conveniently located on the front panel of the nerve integrity monitor. With activation of the push button switch, all (except the quietest) channels with supra threshold levels of repetitive EMG activity are muted from the audio signal to the surgeon. As with the previous "automatic" embodiment, once the activity has quieted to sub-threshold levels, the audio output is automatically re-enabled. It is preferred that the surgeon be given the option of automatic and manual operation by a simple front panel control selections.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method for intraoperative neurophysiological monitoring with at least one electrical stimulus probe as an intraoperative aid in defining the course of a nerve structure by monitoring electromyographic activity within a muscle enervated by the nerve structure, comprising:
   (a) contacting anatomical tissue with the stimulus probe in an area of the nerve structure;
   (b) detecting a change in impedance of the stimulus probe resulting from contact of the stimulus probe with the anatomical tissue;
   (c) triggering a sequence of pre-programmed intraoperative neurophysiological monitoring algorithm steps in response to the detection of the change in impedance of the stimulus probe.

2. The method for intraoperative neurophysiological monitoring of claim 1, wherein step (c) comprises closing a circuit between a current source and the stimulus probe to provide stimulus current to the nerve structure.

3. The method for intraoperative neurophysiological monitoring of claim 1, wherein step (c) comprises:
   (c)(1) generating a visible or audible indication of appropriate impedance of the stimulus probe resulting from contact of the stimulus probe with the anatomical tissue.

4. The method for intraoperative neurophysiological monitoring of claim 1, wherein step (c) comprises:
   (c)(1) initiating generation of a pre-programmed sequence of stimulus pulses to be supplied to the nerve structure via the stimulus probe; and
   (c)(2) storing measured responses to the stimulus pulses collected from an electrode connected to the enervated muscle.

5. The method for intraoperative neurophysiological monitoring of claim 4, further comprising:
   (c)(3) analyzing the stored, measured responses collected from an electrode connected to the enervated muscle, to determine the average response amplitude.

6. The method for intraoperative neurophysiological monitoring of claim 4, further comprising:
   (c)(3) analyzing the stored, measured responses collected from an electrode connected to the enervated muscle, to determine the peak-to-peak response amplitude.

7. The method for intraoperative neurophysiological monitoring of claim 4, further comprising:
   (c)(3) analyzing the stored, measured responses collected from an electrode connected to the enervated muscle, to determine the response threshold.

8. The method for intraoperative neurophysiological monitoring of claim 4, further comprising:
   (c)(3) analyzing the stored, measured responses collected from an electrode connected to the enervated muscle, to determine the response amplitude as a function of stimulus intensity.

9. A method for intraoperative neurophysiological monitoring with at least one electrical stimulus probe as an intraoperative aid in defining the course of a nerve structure by monitoring electromyographic activity within the nerve structure, comprising:
   (a) contacting the nerve structure with the stimulus probe;
   (b) detecting a stimulus probe impedance change resulting from said stimulus probe nerve contact;
   (c) triggering a sequence of pre-programmed intraoperative neurophysiological monitoring algorithm steps in response to the detection of step (b), wherein step (c) comprises:
   (c)(1) generating a visible or audible annunciation of appropriate nerve tissue contact impedance, wherein said step (c) (1) comprises:
   (c)(2) generating an annunciation signal to illuminate a Light Emitting Diode.

10. A method for intraoperative neurophysiological monitoring of an anesthetized patient, comprising:
   (a) placing a first electrode in a muscle of the patient enervated by a selected nerve;
   (b) placing a second electrode in a muscle of the patient not enervated by the selected nerve;
   (c) stimulating the selected nerve;
   (d) monitoring the first electrode for electrical activity and simultaneously monitoring the second electrode for electrical activity; and
   (e) producing an output signal in response to said monitoring including, producing an output signal indicative of artifact if non-repetitive electrical activity is detected at both the first and second electrodes, producing an output signal indicative of an electromyographic response if non-repetitive electrical activity is detected at the first electrode but not at the second electrode, or producing an output signal indicative of potentially inadequate anesthesia if repetitive electrical activity is detected at both the first and second electrodes, wherein said step of producing an output signal indicative of artifact and said step of producing an output signal indicative of an electromyographic response includes producing the output signals if non-repetitive electrical activity of less than about one second is detected, and said step of producing an output signal indicative of potentially inadequate anesthesia includes producing the output signal if repetitive electrical activity of several seconds or more is detected.

11. A method for detecting and analyzing a neurophysiological signal in the body, comprising the steps of:
(a) defining a first probe sampling window of time having a first selected duration;
(b) defining a second probe sampling window of time having a second selected duration and being delayed with respect to said first probe sampling window of time by a selected inter-probe interval of time;
(c) contacting a nerve structure in the body;
(d) sensing a continuous and time varying electromyographic waveform from the nerve structure;
(e) storing said nerve structure electromyographic waveform in memory;
(f) rectifying said nerve structure electromyographic waveform; and
(g) generating a continuous threshold waveform by processing the rectified nerve structure electromyographic waveform through said first probe sampling window and through said second probe sampling window and subtracting the instantaneous value of the waveform power in said second probe window from the instantaneous value of the waveform power in said first probe window.

12. The method for detecting and analyzing a neurophysiological signal of claim 11, further comprising the steps of:
(h) determining whether said continuous threshold waveform includes a first pulse having a first polarity followed by a second pulse having a second polarity by an interval substantially equal to said selected inter-probe interval; and if so,
(i) generating an annunciation indicating that an artifact has been detected.

13. The method for detecting and analyzing a neurophysiological signal of claim 12, further comprising the steps of:
(j) evaluating the distribution among intelligent and non-intelligent electrodes in response to said annunciation that an artifact has been detected.

14. The method for detecting and analyzing a neurophysiological signal of claim 11, further comprising the steps of:
(h) determining whether said continuous threshold waveform includes a first pulse having a pulse width substantially equal to said selected inter-probe interval followed by an interval having no pulse and being substantially equal to said selected inter-probe interval; and if so,
(i) generating an indication that no artifact has been detected.

15. The method for detecting and analyzing a neurophysiological signal of claim 11, wherein said first probe sampling window first selected duration is equal to said second probe sampling window second selected duration.

16. The method for detecting and analyzing a neurophysiological signal of claim 15, wherein said first probe sampling window first selected duration is in the range of 0.25 seconds to 0.5 seconds.

17. The method for detecting and analyzing a neurophysiological signal of claim 15, where said selected inter-probe interval is approximately one second.

18. A method for controlling a neurophysiological monitoring instrument connected to a stimulus probe and one or more electrodes for monitoring electromyographic activity in nerve and muscle structures in the body, comprising:
(a) connecting a first circuit to the stimulus probe for sensing an electrical parameter that changes in response to touching tissue structures in the body, said first circuit being adapted to generate a stimulus probe sensed signal pulse;
(b) connecting a controller connected to said first circuit for receiving said stimulus probe sensed signal, said controller being adapted to execute an algorithm including a plurality of instrument control commands and a plurality of selected patterns of stimulus probe sensed signal pulses;
(c) placing a stimulus probe in proximity to tissue structures in the body;
(d) sensing said electrical parameter changing in response to touching tissue structures in the body;
(e) generating a pattern of stimulus probe sensed signal pulses similar to one of said selected patterns of stimulus probe sensed signal pulses; and
(f) generating an instrument control command in response to detecting said pattern of stimulus probe sensed signal pulses.

19. The method for controlling a neurophysiological monitoring instrument connected to a stimulus probe of claim 18, wherein said instrument control command changes the instrument display mode.

20. The method for controlling a neurophysiological monitoring instrument connected to a stimulus probe of claim 18, wherein said instrument control command changes the instrument stimulus signal amplitude.

21. The method for controlling a neurophysiological monitoring instrument connected to a stimulus probe of claim 18, wherein said instrument control command changes the instrument stimulus signal frequency.

22. The method for controlling a neurophysiological monitoring instrument connected to a stimulus probe of claim 18, wherein said instrument control command begins generation of a predefined pattern of stimulus signal pulses.

23. The method for controlling a neurophysiological monitoring instrument connected to a stimulus probe of claim 18, wherein said instrument control command changes the instrument audible annunciation mode, enabling generation of audible tones.

24. The method for controlling a neurophysiological monitoring instrument connected to a stimulus probe of claim 18, wherein said instrument control command changes the instrument audible annunciation mode, disabling generation of audible tones.

25. The method for controlling a neurophysiological monitoring instrument connected to a stimulus probe of claim 18, wherein said instrument control command causes a command represented by an icon on the instrument display screen to be executed.

* * * * *